(12) United States Patent
Litscher et al.

(10) Patent No.: US 8,062,311 B2
(45) Date of Patent: Nov. 22, 2011

(54) ENDOSCOPIC HEMOSTATIC CLIPPING APPARATUS

(75) Inventors: Eric Litscher, Hopkinton, MA (US); Vincent A. Turturro, Marlboro, MA (US); Roy H. Sullivan, Millville, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1276 days.

(21) Appl. No.: 10/977,598

(22) Filed: Oct. 29, 2004

(65) Prior Publication Data
US 2005/0107809 A1 May 19, 2005

Related U.S. Application Data

(60) Provisional application No. 60/518,167, filed on Nov. 7, 2003.

(51) Int. Cl.
*A61B 17/10* (2006.01)
(52) U.S. Cl. ...................................................... 606/143
(58) Field of Classification Search .................. 606/142, 606/143, 139, 151, 157, 158, 167; 227/19, 227/175.1, 175.2, 175.3, 175.4, 176.1, 177.1, 227/178.1, 181.1, 182.1
See application file for complete search history.

(56) References Cited

U.S. PATENT DOCUMENTS

| 4,627,444 A | 12/1986 | Brooker et al. | |
| 4,733,664 A | 3/1988 | Kirsch et al. | |
| 5,049,152 A * | 9/1991 | Simon et al. | 606/143 |
| 5,049,153 A | 9/1991 | Nakao et al. | |
| 5,156,609 A | 10/1992 | Nakao et al. | |
| 5,366,459 A * | 11/1994 | Yoon | 606/151 |
| 6,599,298 B1 * | 7/2003 | Forster et al. | 606/139 |
| 6,814,742 B2 | 11/2004 | Kimura et al. | |
| 6,843,794 B2 * | 1/2005 | Sixto et al. | 606/142 |
| 7,223,271 B2 * | 5/2007 | Muramatsu et al. | 606/143 |
| 2002/0045909 A1 | 4/2002 | Kimura et al. | |
| 2002/0133178 A1* | 9/2002 | Muramatsu et al. | 606/142 |
| 2002/0151916 A1 | 10/2002 | Muramatsu et al. | |
| 2002/0173786 A1 | 11/2002 | Kortenbach et al. | |
| 2002/0177861 A1 | 11/2002 | Sugiyama et al. | |
| 2002/0198537 A1 | 12/2002 | Smith et al. | |

(Continued)

FOREIGN PATENT DOCUMENTS

AU 2004040289214 5/2005

(Continued)

*Primary Examiner* — Gary Jackson
*Assistant Examiner* — Lindsey Bachman
(74) *Attorney, Agent, or Firm* — Fay Kaplun & Marcin, LLP

(57) ABSTRACT

An apparatus for applying clips to tissue, comprises a plurality of clips, each of the clips including a proximal end having a pair of opposed jaws and a distal end including a linking feature, where the clips are linked to one another to form a clip chain with a linking feature of a distal-most one of the clips being gripped between the jaws of an immediately proximal one of the clips and a control linkage coupled to a proximal-most one of the clips for applying tension and compression to the clip chain in combination with a magazine containing the clip chain, the magazine including an abutment surface sized to prevent passage distally therebeyond of a clip having received between its jaws a linking feature of an immediately distal clip and an opening location within which the jaws of a clip are permitted to open to release a linking feature therefrom.

25 Claims, 27 Drawing Sheets

U.S. PATENT DOCUMENTS

| | | |
|---|---|---|
| 2002/0198538 A1 | 12/2002 | Kortenbach et al. |
| 2002/0198539 A1* | 12/2002 | Sixto et al. .................... 606/142 |
| 2002/0198549 A1 | 12/2002 | Sixto, Jr. et al. |
| 2003/0069592 A1 | 4/2003 | Adams et al. |
| 2004/0138681 A1* | 7/2004 | Pier .............................. 606/143 |
| 2005/0107809 A1 | 5/2005 | Litscher et al. |

FOREIGN PATENT DOCUMENTS

| | | |
|---|---|---|
| WO | 2002/085221 | 10/2002 |
| WO | 2005009254 | 2/2005 |

* cited by examiner

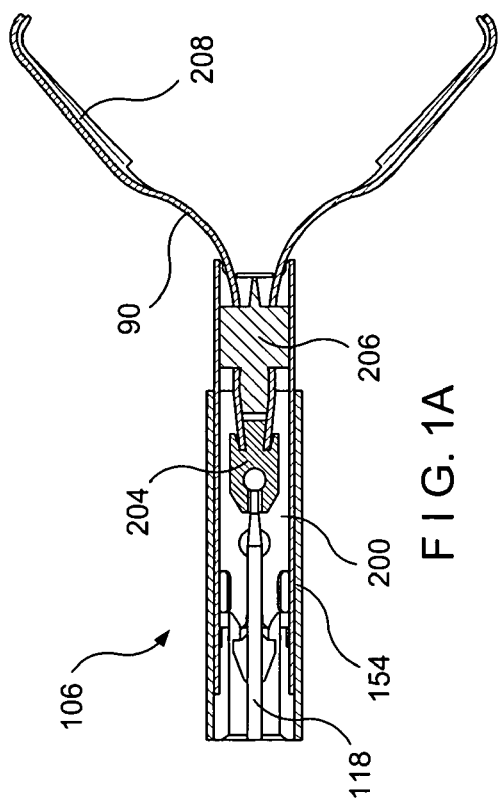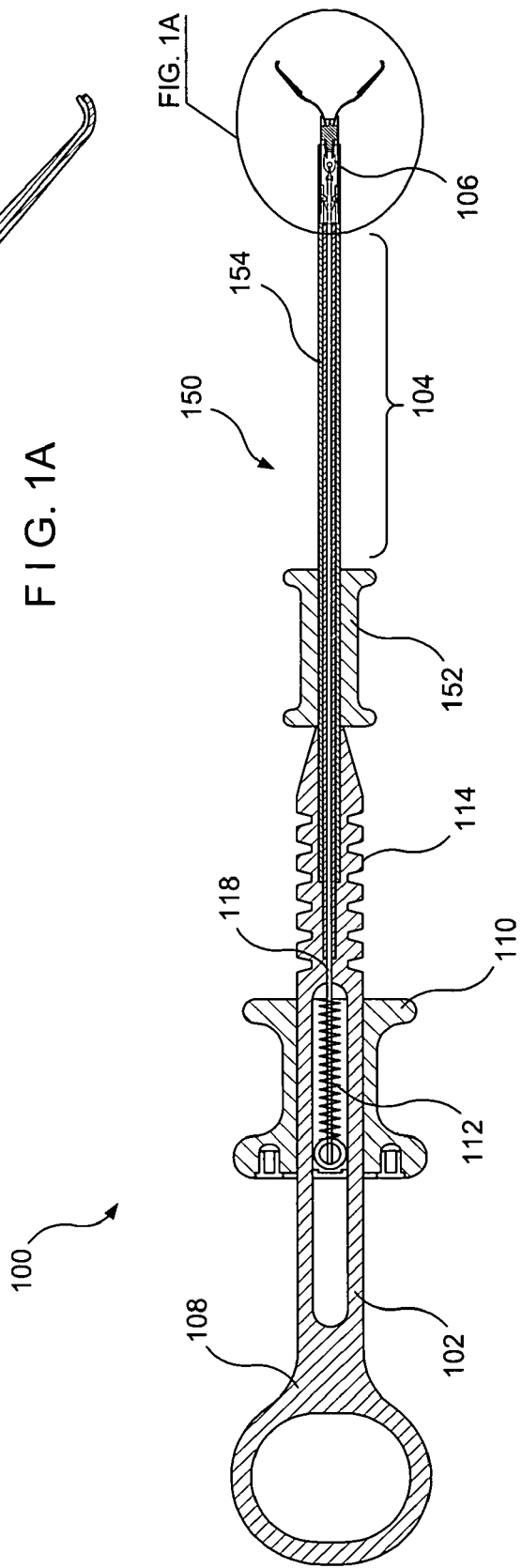

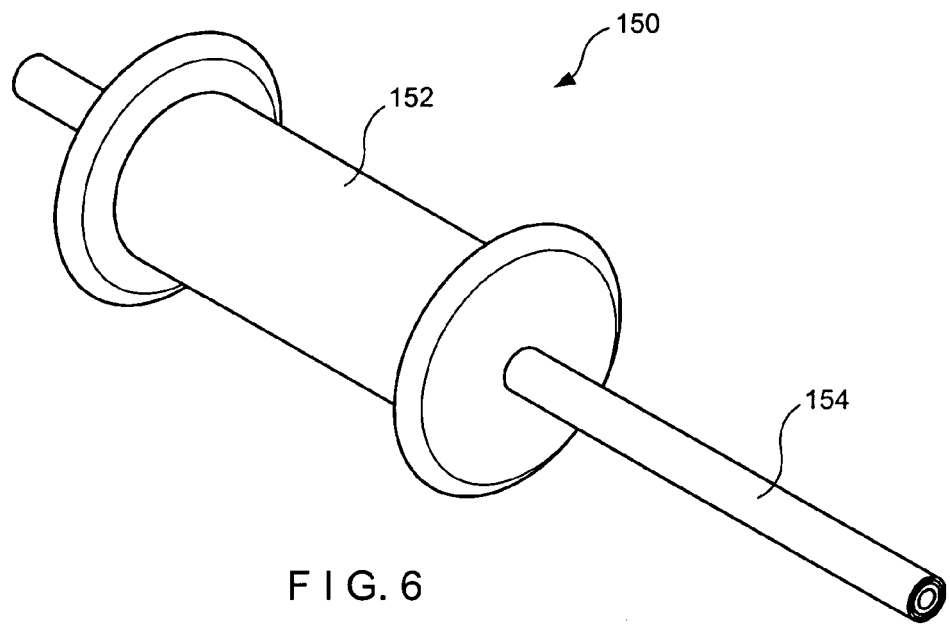
F I G. 6
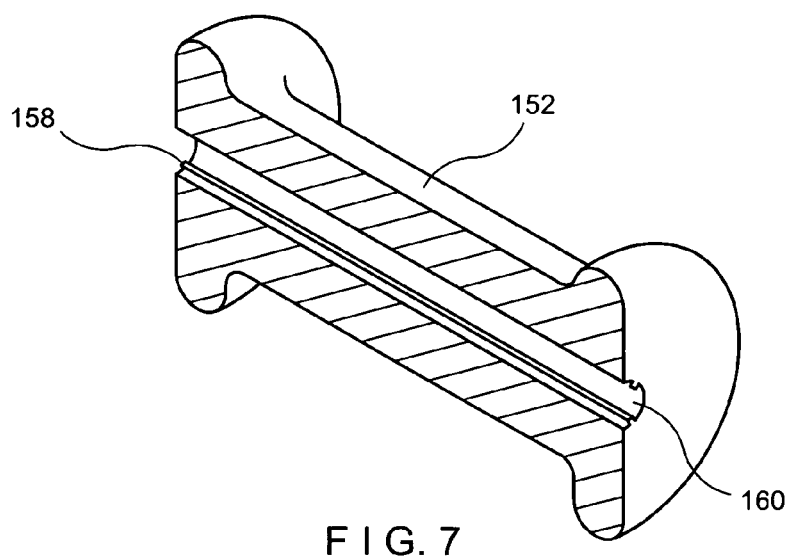
F I G. 7

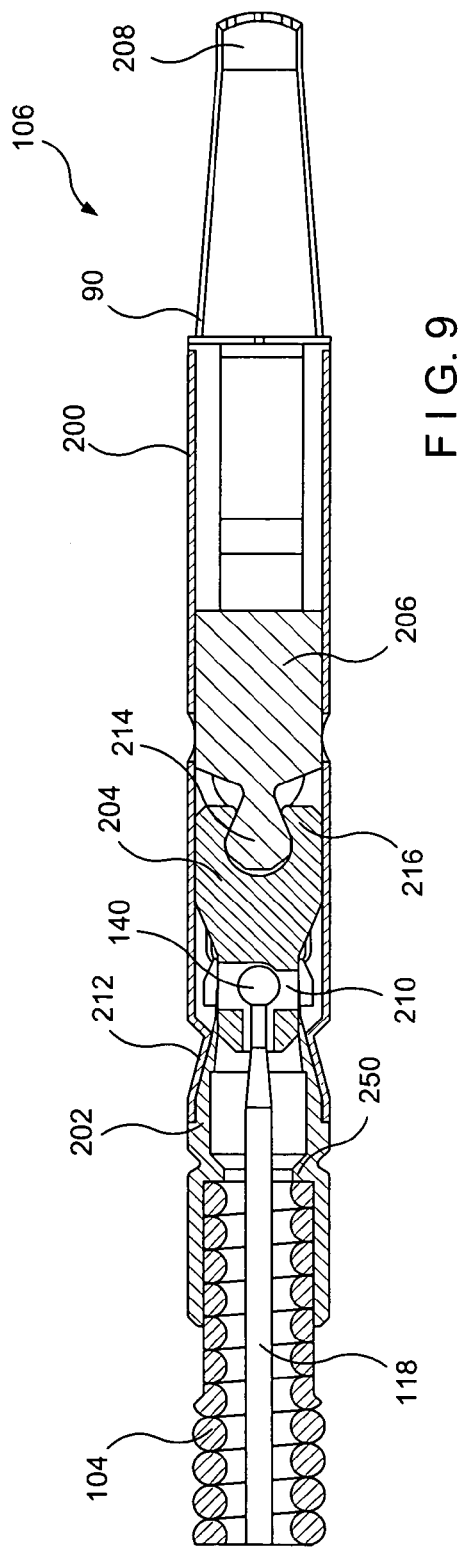
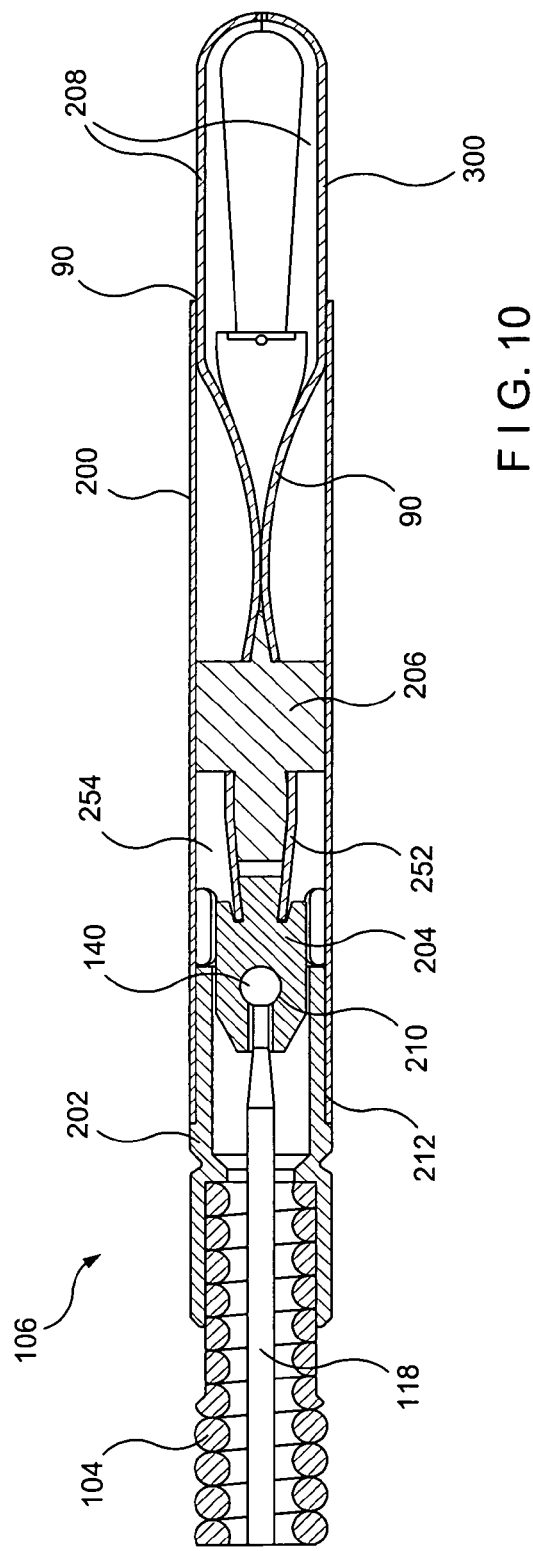
FIG. 9
FIG. 10

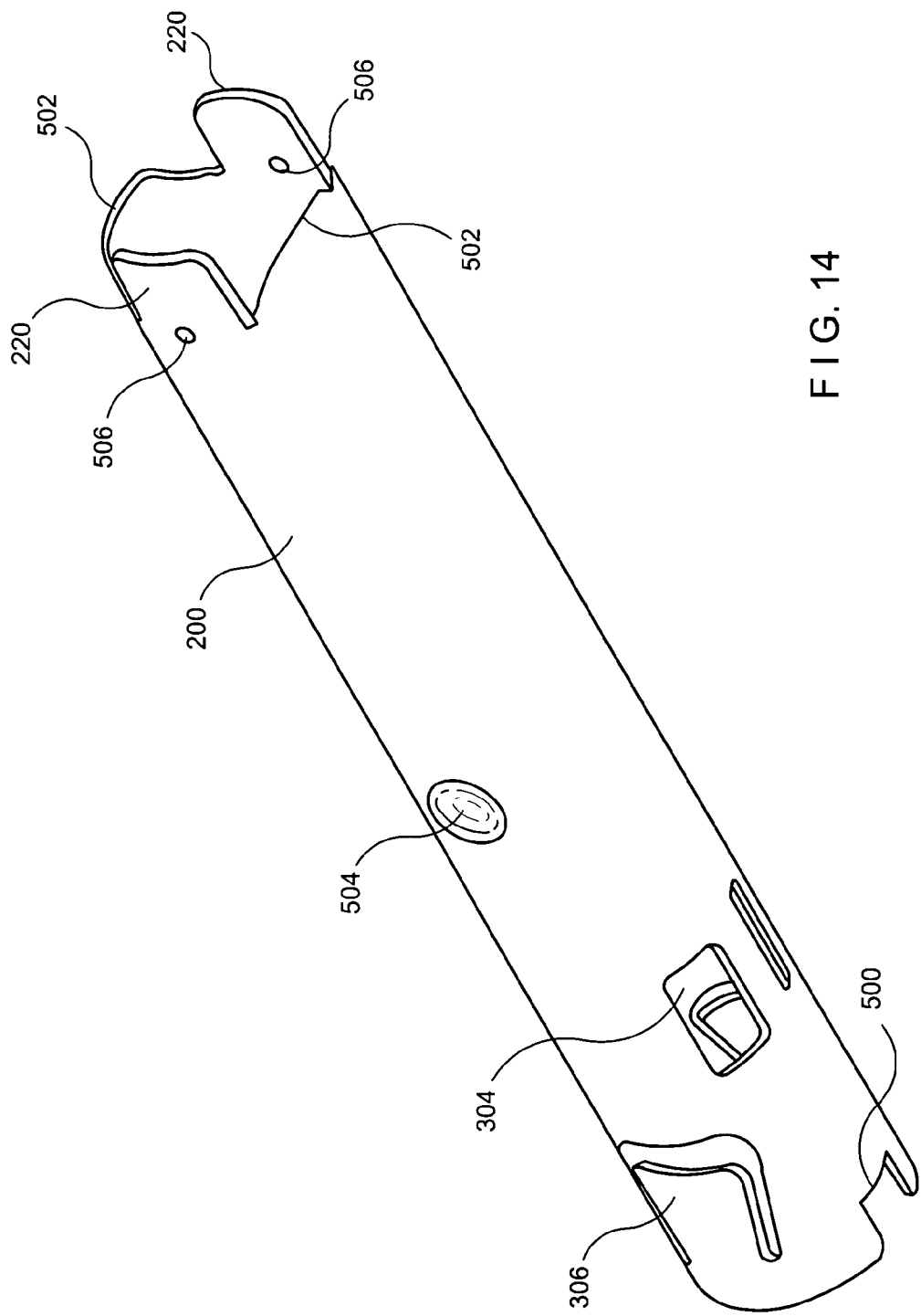
F I G. 14

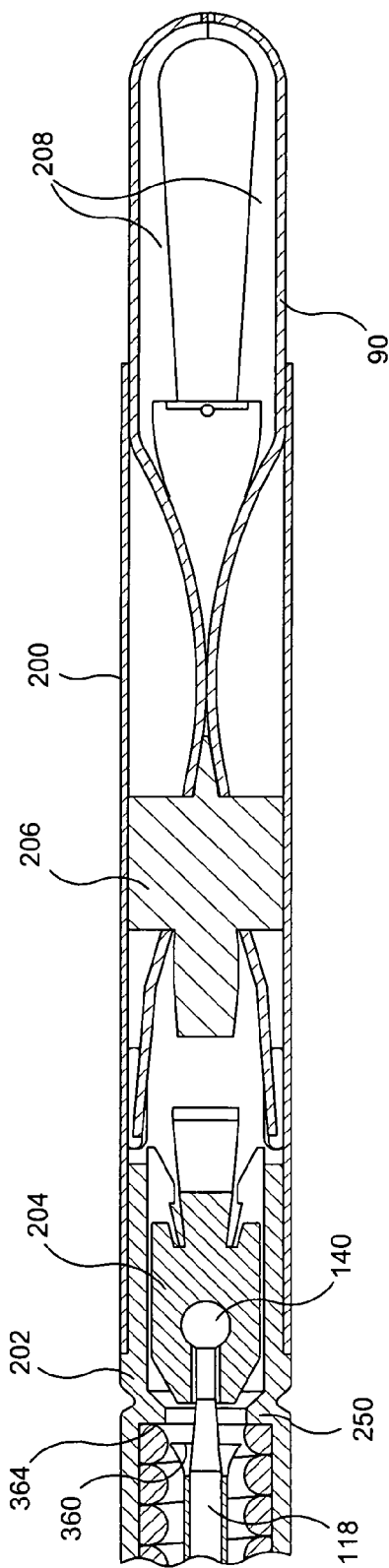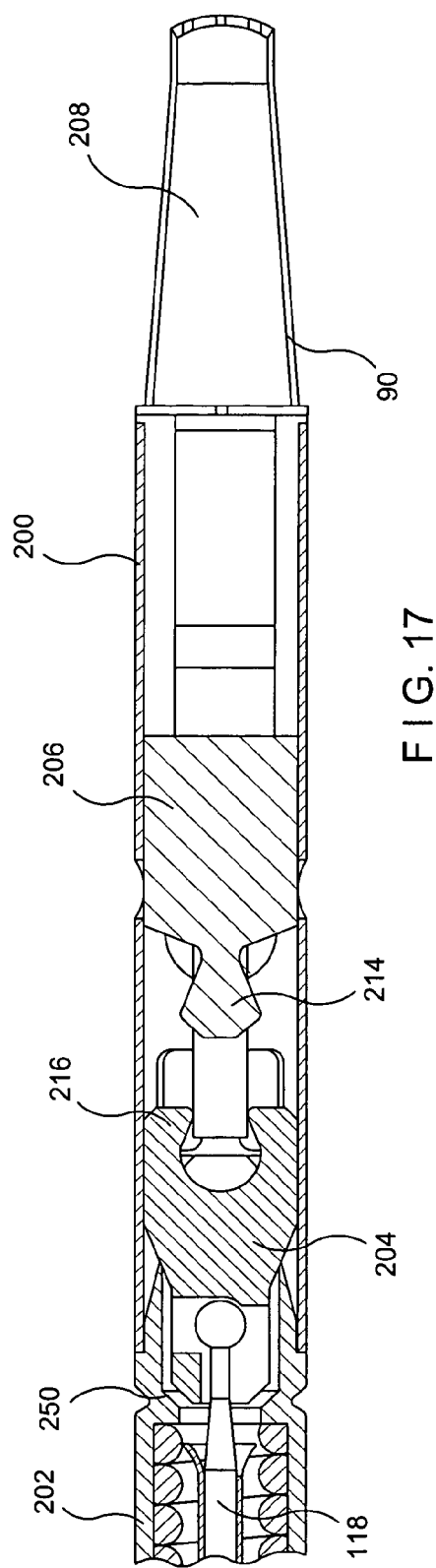
FIG. 16
FIG. 17

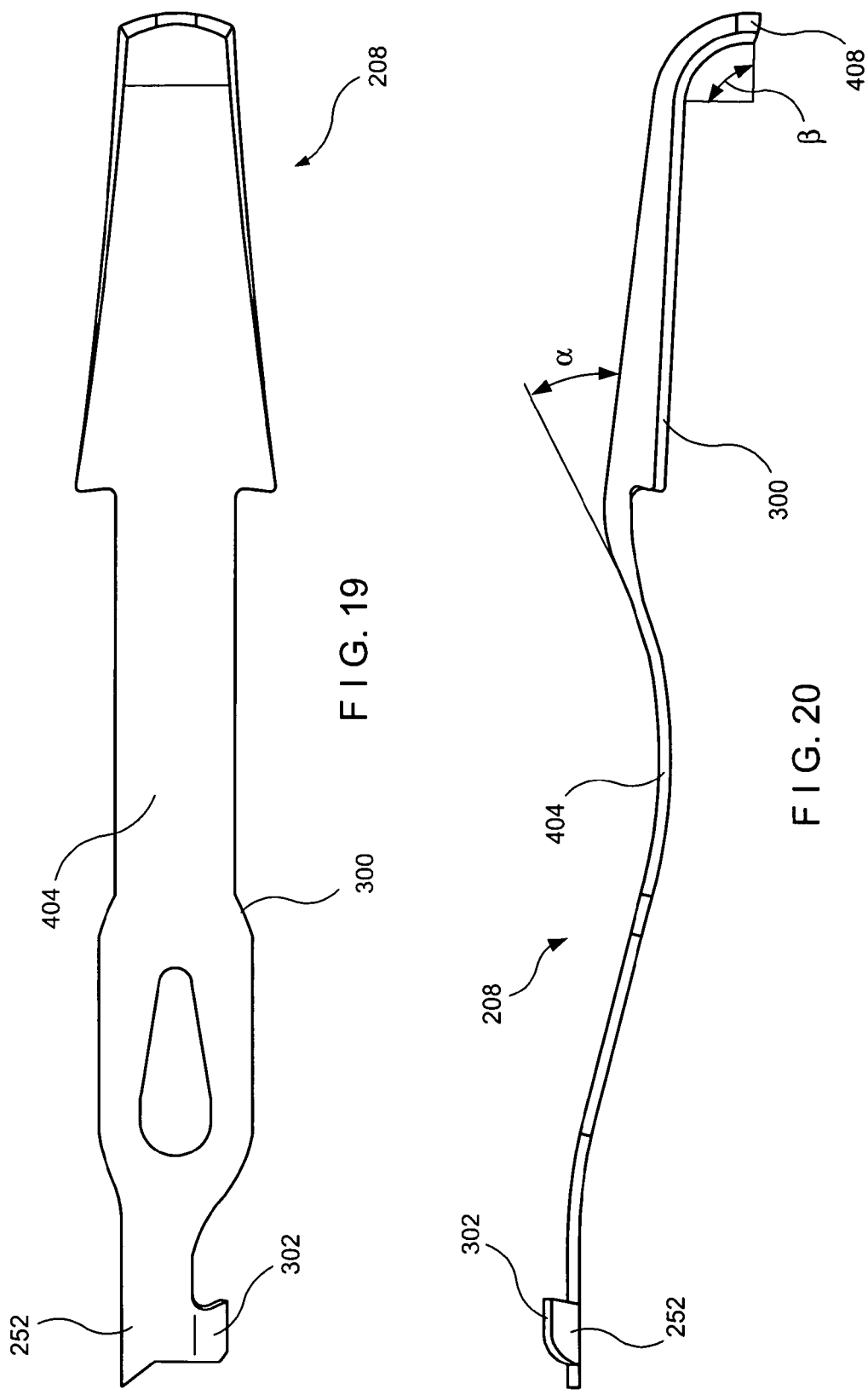

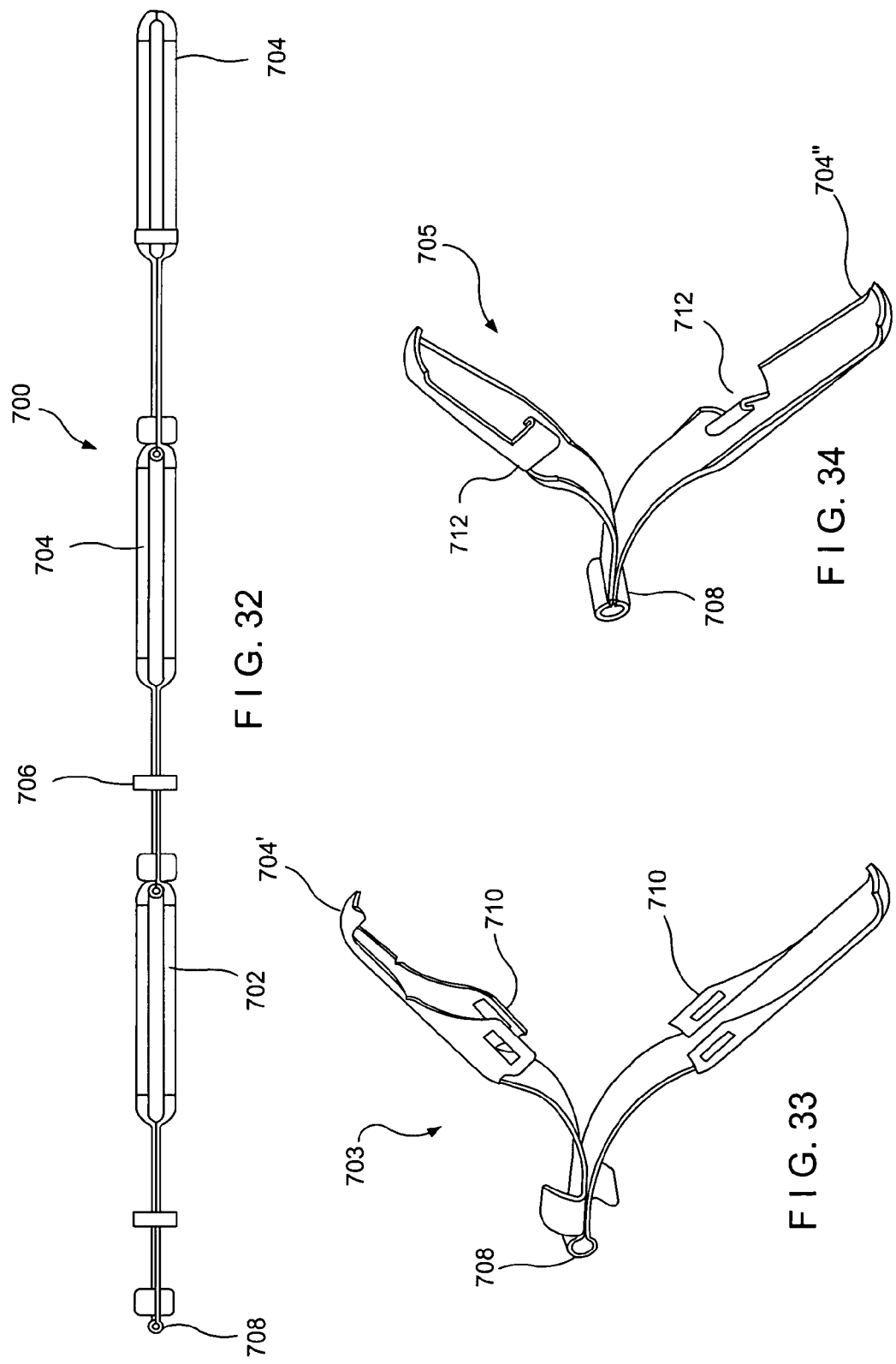

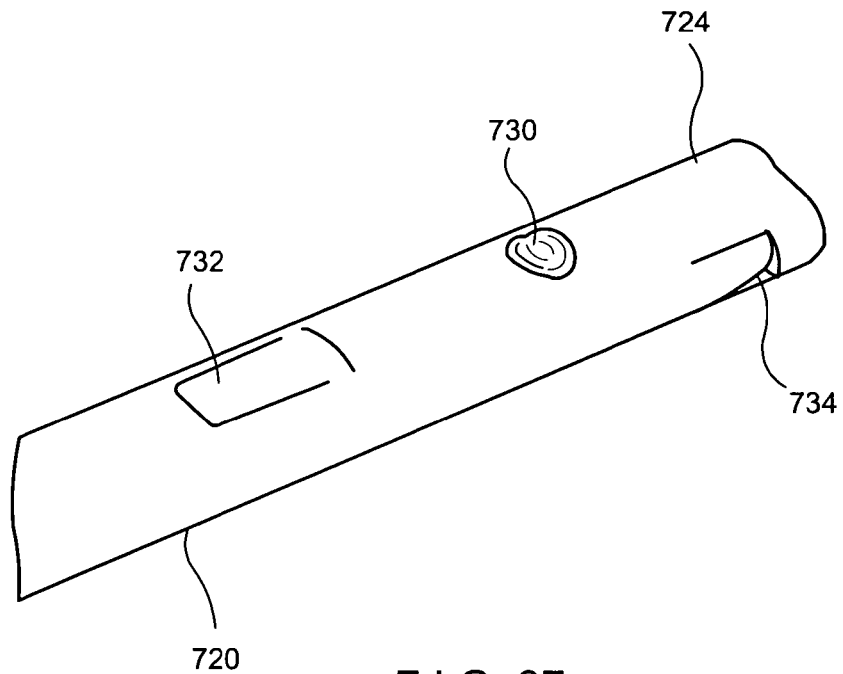
F I G. 37
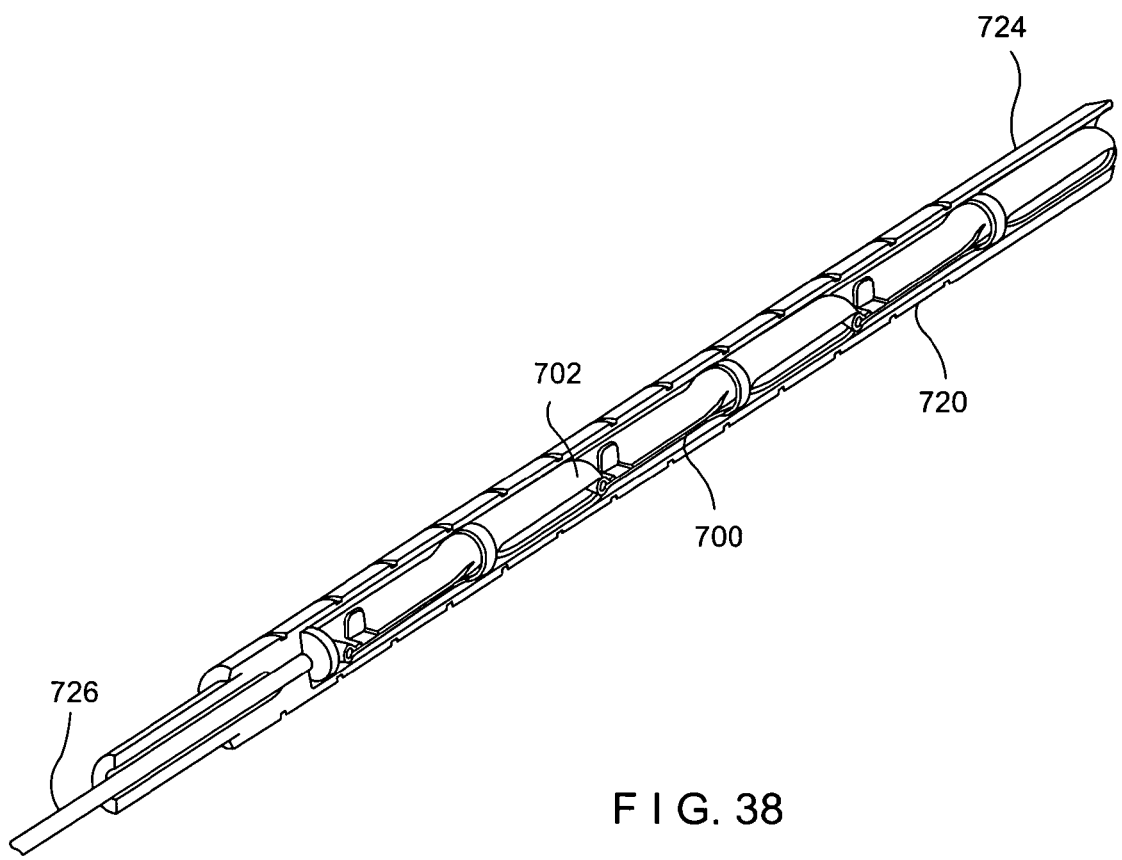
F I G. 38

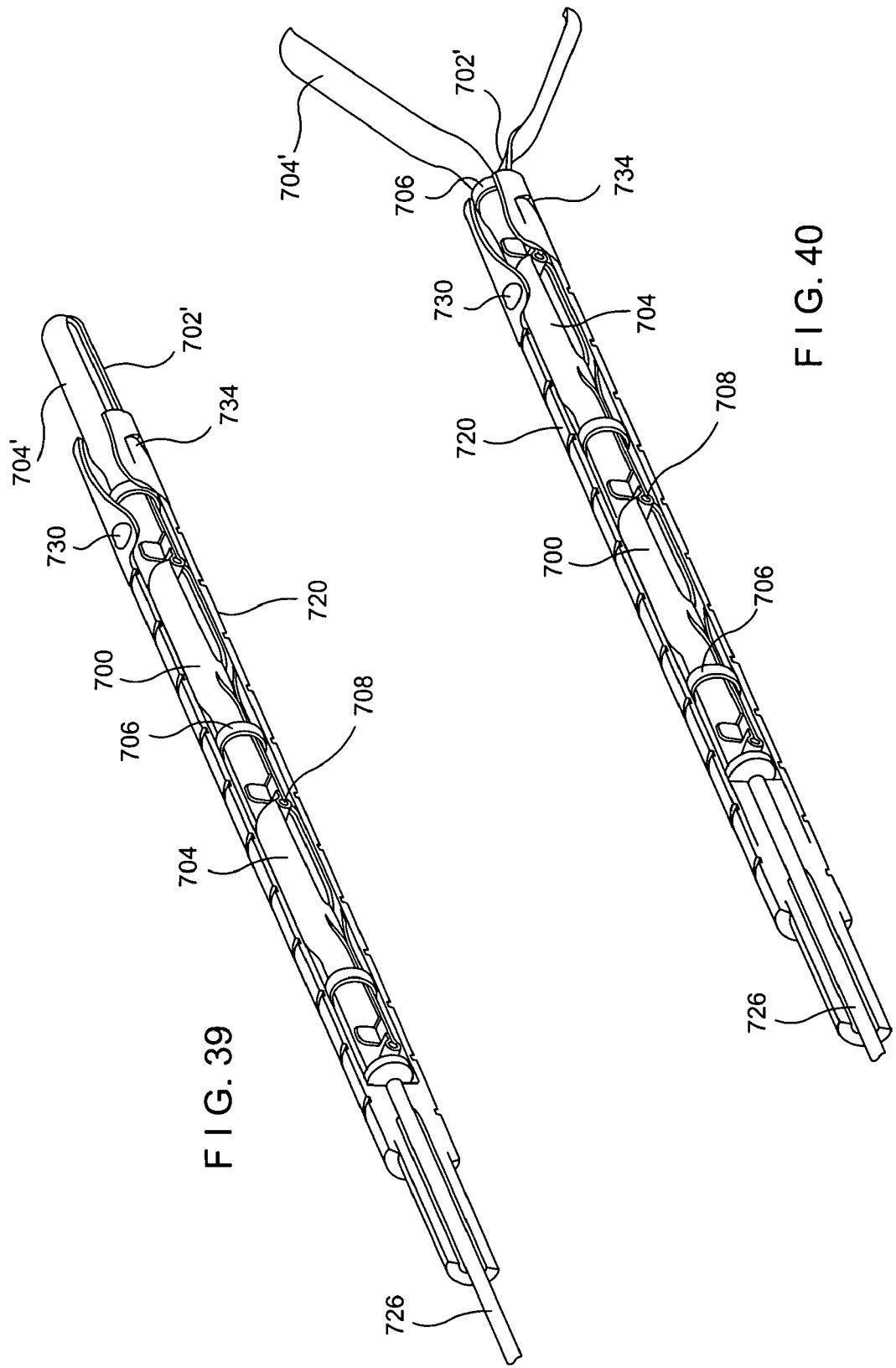

ENDOSCOPIC HEMOSTATIC CLIPPING APPARATUS

PRIORITY CLAIM

Priority is also claimed to U.S. Provisional Patent Application Ser. No. 60/518,167 filed on Nov. 7, 2003 entitled "Endoscopic Multiclip Hemostatic Clipping Apparatus." The entire disclosure of the prior application is considered as being part of this disclosure and is expressly incorporated by reference herein.

BACKGROUND

Endoscopic procedures to treat pathologies of the gastrointestinal ("GI") system, the biliary tree, the vascular system and other body lumens are becoming increasingly common. The endoscope, which is basically a hollow tube placed at a desired location within the body to facilitate access to body ducts and lumens, etc. is unable to carry out many procedures on its own. Additional devices are often inserted to the target site through lumens or working channels of the endoscope to perform the desired treatment via controls which remain outside the body.

A hemostatic clipping tool is one of the devices which may be inserted through an endoscope to deploy a clip to stop internal bleeding by clamping together the edges of a wound. A clipping tool complete with a clip attached to its distal end is inserted through the endoscope to the location of the wound and the clip is then remotely manipulated into position over the site of the bleeding, clamped over the wound and detached from the tool. After a number of clips sufficient to stop the bleeding has been deployed, the tool is withdrawn through the endoscope. The size and shape of the clips and clipping tool are limited by the inner diameter of the lumen(s) of the endoscope placing constraints on the design of clip positioning and release mechanisms which may be employed.

At times it may be difficult to properly position hemostatic clips over a wound. When clips are improperly deployed, additional clips may be required to stop the bleeding, extending the time required for and the complexity of the procedure while leaving additional medical devices within the patient. It is also important that the device operator be certain of the status of the clip during the deployment operation. For example, before withdrawing the tool from the endoscope, the operator should have a positive indication that a clip has fully deployed and has been released from the tool. At the same time the design of the tool should ensure that clips are fully released after they have been closed over the tissue.

SUMMARY OF THE INVENTION

In one aspect, the present invention is directed to an apparatus for applying clips to tissue, comprising a plurality of clips, each of the clips including a proximal end having a pair of opposed jaws and a distal end including a linking feature, where the clips are linked to one another to form a clip chain with a linking feature of a distal-most one of the clips being gripped between the jaws of an immediately proximal one of the clips and a control linkage coupled to a proximal-most one of the clips for applying tension and compression to the clip chain in combination with a magazine containing the clip chain, the magazine including an abutment surface sized to prevent passage distally therebeyond of a clip having received between its jaws a linking feature of an immediately distal clip and an opening location within which the jaws of a clip are permitted to open to release a linking feature therefrom.

The present invention is further directed to a method of deploying hemostatic clips, comprising inserting to a target site in a body a magazine including a plurality of hemostatic clips connected in a clip chain, translating the clip chain distally to extend a distal-most one of the clips out of a distal end of the magazine to open clip arms of the distal-most clip into a tissue receiving configuration and positioning the distal-most clip to receive a first target portion of tissue between the clip arms thereof in combination with translating the clip chain proximally to draw the distal-most clip back into the magazine and close the clip arms of the distal-most clip over the first target portion of tissue and translating the clip chain further proximally to detach the distal-most clip from a next most distal clip of the clip chain. Then, the magazine is moved to a second target location to deploy the next most distal clip over a second target portion of tissue.

BRIEF DESCRIPTION OF THE DRAWINGS

FIG. 1 is a schematic side view of a clipping device according to an embodiment of the present invention, with a detail view of an exemplary clip assembly;

FIG. 6 is a perspective view of an outer sheath according to an embodiment of the present invention;

FIG. 7 is an cross sectional exploded view of the handle of the outer sheath shown in FIG. 6;

FIG. 9 is a cross sectional side view of a distal end of a clipping device according to an embodiment of the present invention;

FIG. 10 is a cross sectional top view of a distal end of the clipping device shown in FIG. 9;

FIG. 14 is a perspective view of a capsule according to an embodiment of the present invention;

FIG. 16 is a top view of the distal end of a clipping device according to an embodiment of the present invention;

FIG. 17 is a side view of the distal end shown in FIG. 16;

FIG. 19 is a side view of the clip arm shown in FIG. 18;

FIG. 20 is a top view of the clip arm shown in FIG. 18;

FIG. 32 shows a side elevation view of a clip chain according to an embodiment of the invention;

FIG. 33 shows a perspective view of a second embodiment of a clip for a clip chain according to the invention;

FIG. 34 shows a perspective view of a third embodiment of a clip for a clip chain according to the invention;

FIG. 37 shows a distal end detail of the clip magazine shown in FIG. 36;

FIG. 38 shows a cut away perspective view of a clip chain loaded in a clip magazine according to an embodiment of the invention;

FIG. 39 shows the clip chain of FIG. 38 being pushed out of the clip magazine;

FIG. 40 shows the clip chain of FIG. 38 yet further out of the clip magazine with one clip deployed;

DETAILED DESCRIPTION

Figure 2:
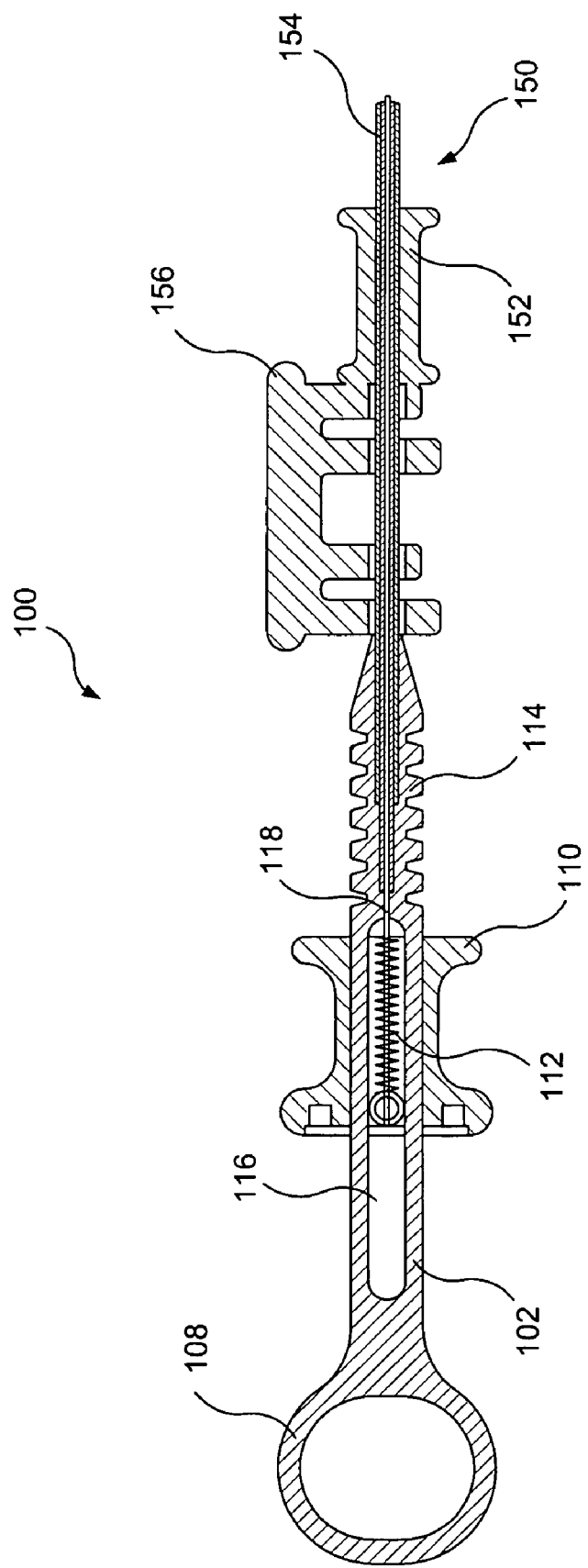
FIG. 2 is a schematic side view of the embodiment shown in FIG. 1, with a outer sheath.

Hemostatic clips are routinely used to stop internal bleeding. In the simplest form, these clips grasp tissue surrounding a bleeding opening and bring the edges together to allow the natural scarring process to close the opening. Specialized endoscopic hemostatic clipping devices are used to bring clips to desired locations within the body and to position and deploy clips at appropriate places on the tissue. The clipping device is then withdrawn, leaving the clip(s) within the patient. One such hemostatic clipping devices is described in U.S. patent application Ser. No. 10/647,512, filed on Sep. 30, 2003, and entitled THROUGH THE SCOPE TENSION MEMBER RELEASE CLIP, assigned to the assignee of the present application, which is hereby incorporated herein by reference in its entirety.

As described above, endoscopic hemostatic clipping devices are designed to reach affected tissues deep within a patient's body, such as within the GI tract, the pulmonary system, the vascular system or within other lumens and ducts. During the procedures to treat those areas, an endoscope is generally used to provide access to and visualization of the tissue which is to be treated. The clipping device may, for example, be introduced through a working lumen of the endoscope. The design and construction of such a "through the scope" endoscopic hemostatic clipping device presents several challenges. The endoscopic clipping device has to be sufficiently small to fit in the lumen of an endoscope and, at the same time, must be designed to provide for the positive placement and actuation of the hemostatic clip. Feedback to the operator is preferably also provided so that the operator will not be confused as to whether the hemostatic clip has been properly locked in place on the tissue and released from the device before the device itself is withdrawn through the endoscope.

FIG. 1 shows a side elevation view of a through the scope hemostatic clipping device according to an exemplary embodiment of the present invention. This device is a hand operated tool that is used to insert a hemostatic clip through an endoscope lumen, position the clip over a wound, clamp it and deploy it over the affected tissue. The tool is further designed to release the hemostatic clip once it has been clamped in place, and to be withdrawn through the endoscope. To more clearly explain the operation and construction of the exemplary device, it may be divided into three principal components. As shown, the hemostatic clipping device 100 comprises a handle assembly 102, a shaft section 104, and a clip assembly 106. The clip assembly 106 is shown more clearly in FIG. 1A.

The handle assembly 102 forms the component that supplies a mechanical actuation force to deploy and clamp the clip. In this embodiment, the device is hand operated (i.e., the user's hands provide the force required to carry out all the functions related to the hemostatic clip). However, those skilled in the art will understand that the handle assembly 102 may include or be coupled to a power source such as a motor or hydraulic pump which may be connected to the distal end of the shaft section 104 by known mechanisms to effect operation of the device. The handle assembly 102 may be constructed in a manner similar to conventional handle assemblies of the type generally employed in endoscopic biopsy devices or in similar applications. The handle assembly 102 allows the user to move a control wire 118 or other force transmission member, which extends through the shaft section 104 to the clip assembly 106 at a distal end of the device 100. The handle assembly 102 comprises a handle body 108 which can be grasped by the user to stabilize the device and apply a force to it. A sliding spool 110 is connected to control wire 118, so that the user can easily pull or push said wire 106 as desired.

As shown in FIGS. 1 and 2, a sliding spool 110 is mounted on the handle body 108 so that it may slide along a slot 116, which maintains its position within the handle assembly 102. Because the sliding spool 110 is connected to the control wire 118, the user may manipulate the control wire 118 by grasping the handle body 108 and moving the sliding spool 110 along the slot 116. A return spring 112 may be provided within the handle body 108 to bias the sliding spool 110, and thus the control wire 118 toward a desired position. In the present embodiment, the sliding spool 110 is biased to the proximal position. The handle assembly 102 also includes a connection portion 114, which receives the control wire 118 and attaches the shaft section 104 to the handle assembly 102.

Figure 4:
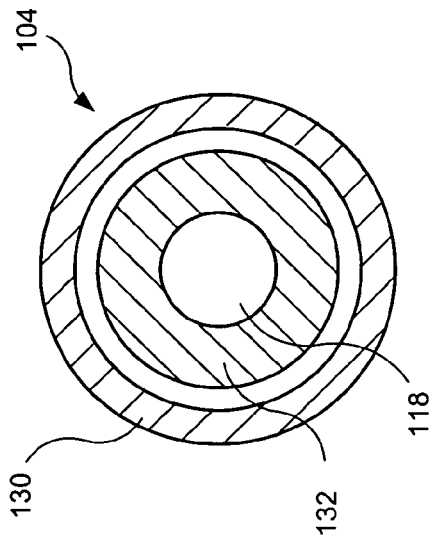
FIG. 4 is a cross sectional view of the shaft section shown in FIG. 3.
Figure 3:
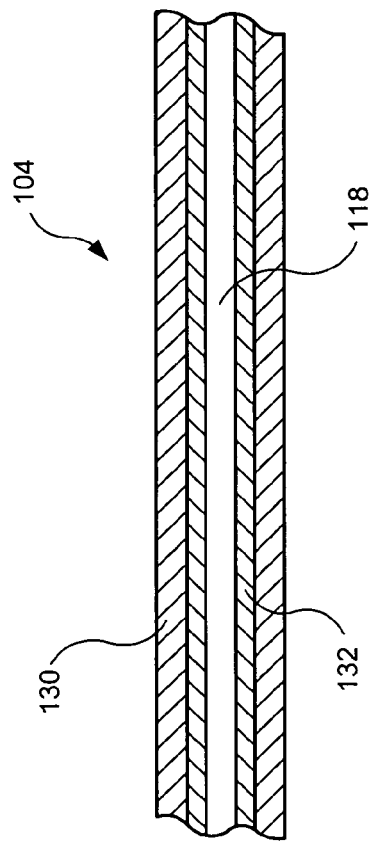
FIG. 3 is a cut away side view of the shaft section according to an embodiment of the present invention.

The shaft section 104 mechanically connects the handle assembly 102 to the clip assembly 106 and, together with the clip assembly 106, is designed to be inserted to a target site within a body via a lumen of an endoscope. As shown in FIGS. 3 and 4, the shaft section 104 comprises an outer flexible coil 130 designed to transmit a torque from the proximal end to the distal end of the device 100 and to provide structural strength to the shaft section 104. The coil 130 may be a conventional coil used in biopsy devices and may, for example, comprise a single, coiled wire. The coiled wire may have a round, square or a rectangular cross section, and is preferably composed of a biocompatible material such as, for example, stainless steel. Additional protective and low friction outer layers may be included on the shaft section 104, according to known methods of construction.

Figure 5:
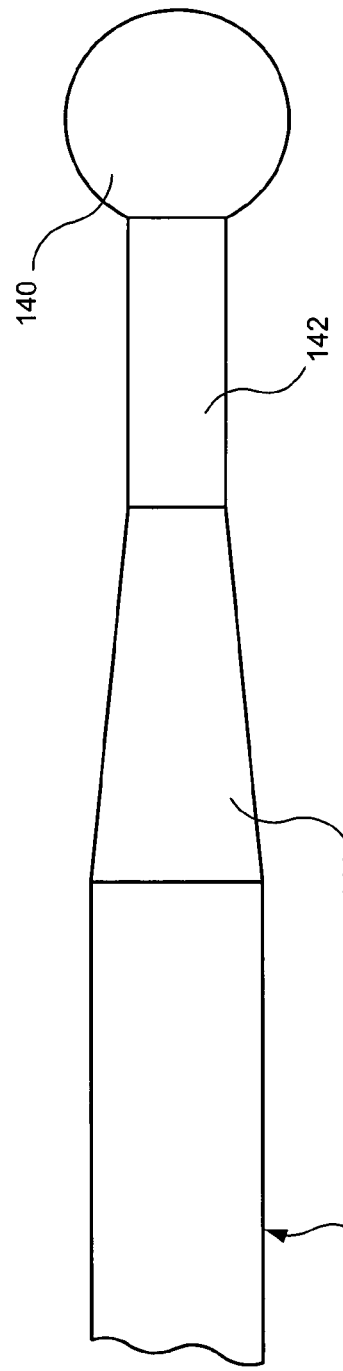
FIG. 5 is a detail view of the distal end of the control wire according to an embodiment of the present invention.

The control wire 118 transmits mechanical force applied to the handle 102 to the clip assembly 106. The control wire 118 has a proximal end attached to a movable part of the handle 102, such as the sliding spool 110, using known methods. Stainless steel or other high yield biocompatible materials may be used to manufacture the control wire 118, so that the structural integrity of the assembly is maintained. It is also important to prevent stretching of the control wire 118 when under tension since, if the wire stretches, the handle 102 will have to travel a greater distance to carry out a desired operation. As shown in FIG. 5, the distal end of the control wire 118 ends in a ball 140 which is used to connect the control wire 118 to the appropriate elements of the clip assembly 106, as will be described below. In this embodiment, the diameter of the control wire 118 is substantially constant from a proximal end thereof to a proximal end of a distal tapered section 144. The ball 140 preferably has a diameter greater than a diameter of a reduced diameter section 142 coupled to a distal end of the distal tapered section 144 and more preferably has a diameter greater than the proximal portion of the control wire 118, to facilitate attachment to a yoke 204. The control wire 118 extends the length of the device 100, from the yoke 204 to the sliding spool 110, and is designed to slide longitudinally along the device 100.

The control wire 118 also preferably includes a selected failure zone (e.g., reduced diameter section 142) designed to fail when a predetermined tension is applied thereto through the handle assembly 102. The tapered section 144 may be used to transition between the main body of the control wire 118 and the reduced diameter section 142, without steps or other discontinuities which may concentrate stress and make the fracture point more unpredictable. As will be described in greater detail below, one purpose of the reduced diameter section 142 is to facilitate the release of a hemostatic clip from the hemostatic clipping device 100 once the clip has been properly deployed. It will be apparent to those of skill in the art that the location of the reduced diameter section 142 the along control wire 118 may be varied to take into account specific requirements of the device 100.

An inner sheath 132 may be used in the construction of the shaft section 104, as shown in FIGS. 3 and 4. The inner sheath 132 provides a low friction bearing surface disposed between the outer diameter of the control wire 118, and the inner diameter of the shaft section 104. The inner sheath 132 may be formed of a low friction material such as, for example, Teflon™, HDPE or Polypropylene. In one exemplary embodiment, the inner sheath 132 is slidable within the shaft section 104, and the control wire 118 is slidable within the inner sheath 132 forming a low friction system of multiple bearing surfaces. To further reduce friction, a bio-compatible lubricant may be applied to the inner and outer surfaces of the inner sheath 132, along the length of the shaft section 104. For example, silicone lubricants may be used for this purpose.

A slidable over-sheath 150 may be included in the design of the shaft section 104, as shown in FIGS. 1 and 2. The over-sheath 150 is designed to protect the inner lumen of the endoscope from the metal clip assembly 106 and from the metal coil 130 while the hemostatic clipping device 100 passes through the endoscope's lumen. After the clipping device 100 and, more specifically, after the clip assembly 106 has passed through the endoscope, the over-sheath 150 may be withdrawn to expose the distal portion of the clipping device 100. The over-sheath 150 may be formed, for example, as a single lumen plastic extrusion element slidable over the distal portions of the clipping device 100 to selectively cover and uncover the clip assembly 106. In one embodiment, the over-sheath 150 is formed of a low friction polymer such as, for example, Teflon™, HDPE, Polypropylene, or similar materials.

The over-sheath 150 may include a grip portion 152 and an elongated body 154. The grip portion 152 is designed as a handle making it easier for the user to slide the over-sheath 150 over the shaft of the clipping device 100. In one exemplary embodiment, the grip portion 152 is made of a rubber-like material to provide a good gripping surface for the user. For example, an injection moldable polymer such as TPE may be used to construct the grip portion 152. The elongated body 154 may be formed as a substantially cylindrical shell surrounding the shaft of the clipping device 100. The elongated body 154 may be attached to the grip portion 152 using conventional methods as would be understood by those skilled in the art.

As shown in FIGS. 6 and 7, an exemplary grip portion 152 comprises a central hollow channel 160 that may be used to receive the shaft of the clipping device 100. The central hollow channel 160 is aligned with the elongated body 154 to provide a continuous channel containing the shaft of the clipping device 100. The material of the grip portion 152 preferably has a high coefficient of friction, so that an interference fit is possible between the central hollow channel 160 and the shaft of the clipping device 100 without the use of adhesives or mechanical fastening devices. In one embodiment, friction bosses 158 are provided on an inner diameter of the hollow channel 160 to provide additional friction between the shaft of the clipping device 100 and the over-sheath 150 assembly. The friction bosses 158 may be formed, for example, as protrusions extending from the inner diameter of the over-sheath 150 and may have a variety of stubby or elongated shapes. The amount of friction between these two components may be balanced so that no unwanted relative movement takes place while, at the same time, making it relatively easy for the user to slide the over-sheath 150 proximally and distally when necessary.

Figure 8:
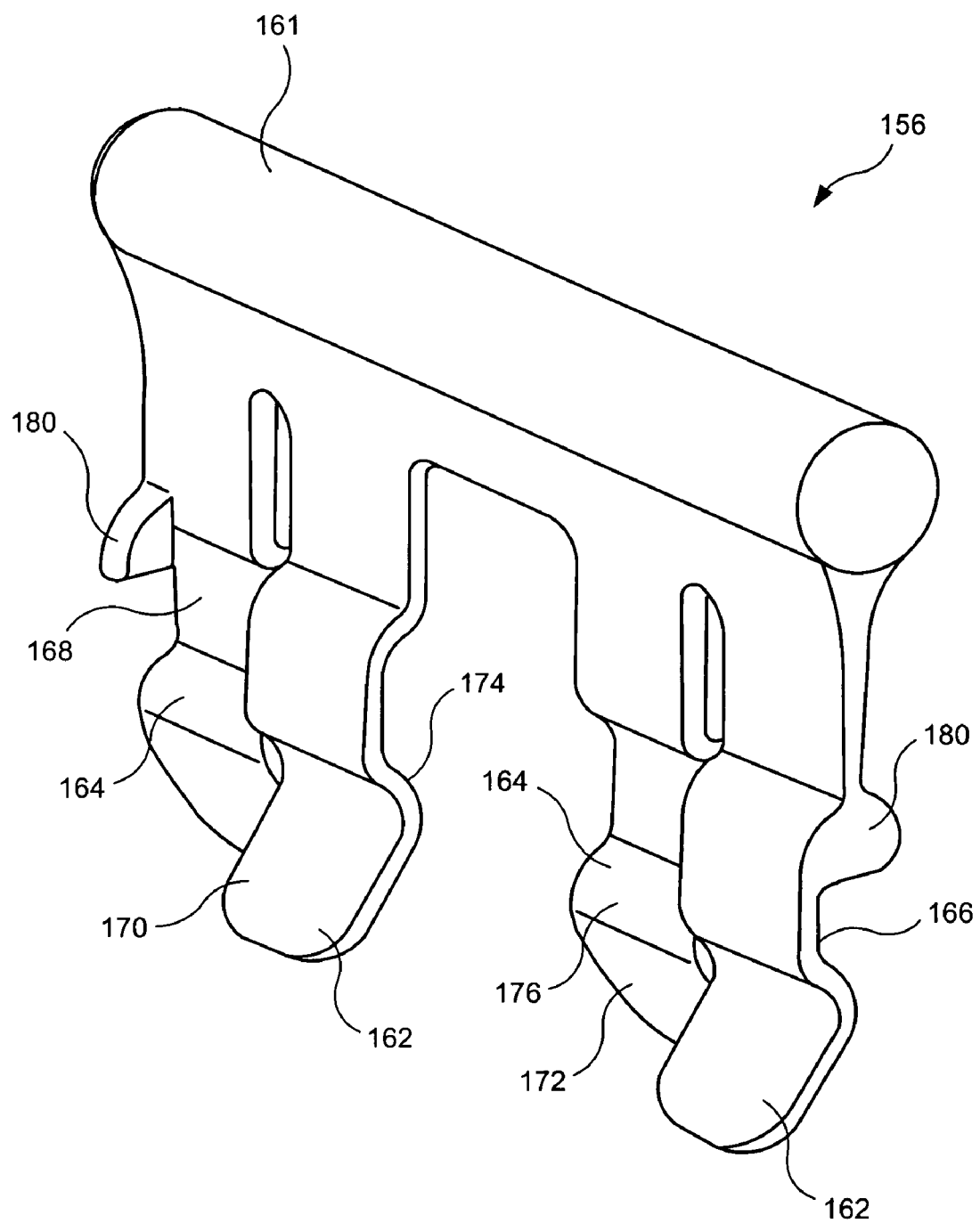
FIG. 8 is a perspective view of an outer sheath lock according to an embodiment of the present invention.

A sheath stop 156 may be provided to prevent the over-sheath 150 from sliding away from the distal end while the clipping device 100 is inserted in the endoscope. As shown in the exemplary embodiment of FIGS. 2 and 8, the sheath stop 156 physically blocks the grip portion 152 from sliding proximally to prevent the over-sheath 150 from being withdrawn and exposing the clip assembly 106. The sheath stop 156 is designed to easily snap into place near the proximal end of the shaft section 104 where it can be reached and manipulated by the operator during the surgical procedure. Once the clip assembly 106 has been inserted through the endoscope to the desired location in the body, the sheath stop 156 may be removed from the shaft section 104 so that the user can move the grip portion 152 proximally to uncover the clip assembly 106.

The connection between the sheath stop 156 and the shaft section 104 may include, for example, pairs of opposing fingers 162, 164 that are designed to snap over the shaft section 104. The fingers 162, 164 cooperate to securely and releasably hold the body of the shaft section 104 therebetween. The fingers 162, 164 respectively comprise guide portions 170, 172; shaft channel portions 166, 168; and blocking portions 174, 176. Insertion of the sheath stop 156 on the elongated body 154 is accomplished by pressing the body of the shaft section 104 between the guide portions 170, 172, to spread the fingers 162, 164 and allow further insertion of the shaft 104 between the fingers 162, 164. The guide portions 170, 172 and the blocking portions 174, 176 are shaped so that insertion of the shaft section 104 towards the channel portions 166, 168 requires less effort than moving the shaft section 104 in the opposite direction.

Once shaft section 104 has been placed within the channel portions 166, 168, the fingers 162, 164 snap back to their non-spread position and retain the shaft section 104 in place therebetween. The shaft section 104 is removed by pulling the sheath stop 156 away from the shaft section 104. Due to the shape of the blocking portions 174, 176, removing the shaft section 104 requires the application of more force than does insertion thereinto. Stops 180 may also be provided on the sheath stop 156 to limit the movement of the shaft section 104 towards the grasping portion 161 to prevent damage to the device that may be caused by excessive spreading of the fingers 162, 164. The sheath stop 156 is preferably formed of a resilient material, such as a polymer, and may be manufactured, for example, by injection molding.

Figure 11:
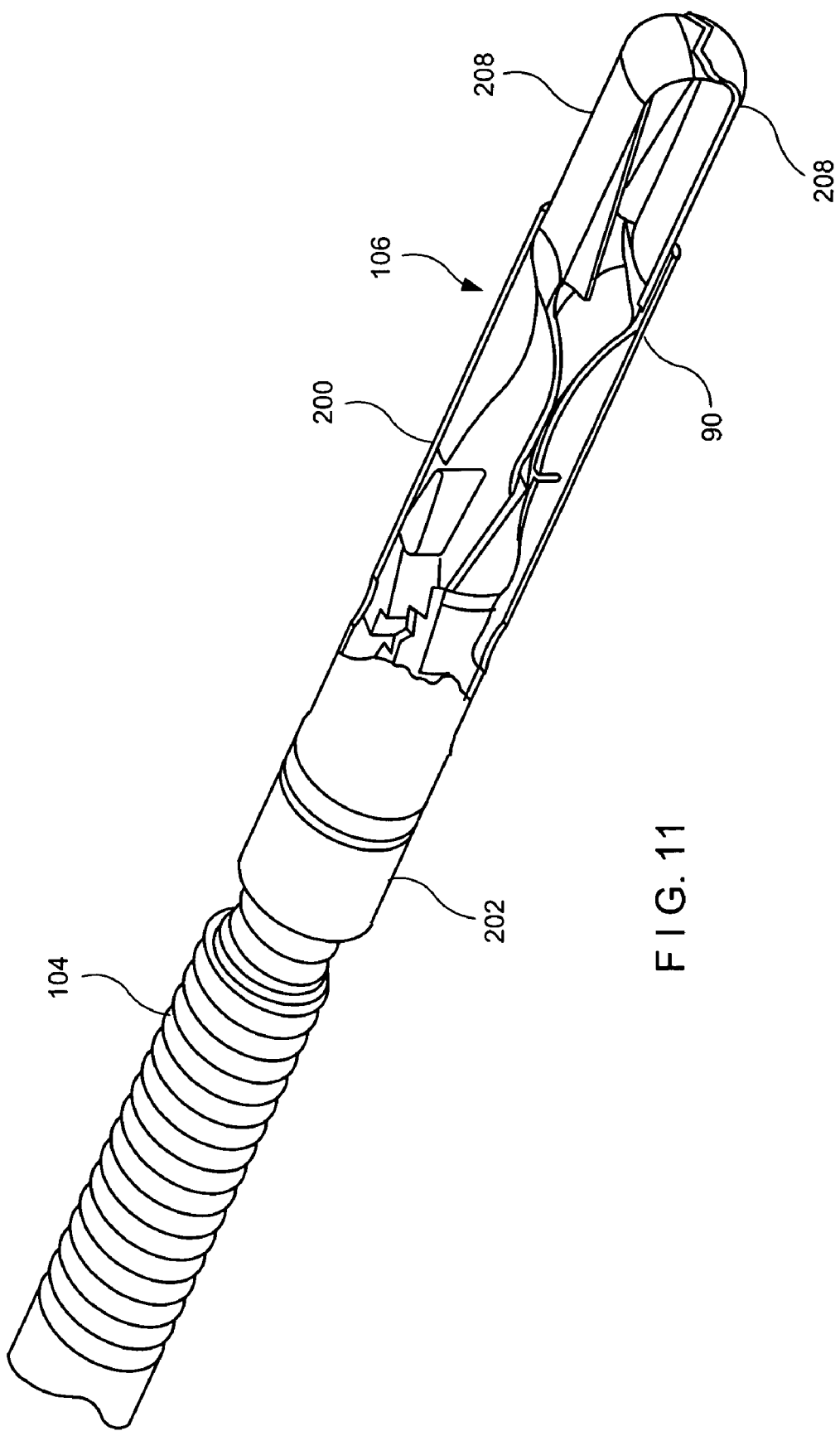
FIG. 11 is a perspective view of the distal end of the clipping device shown in FIG. 9.

The clip assembly 106 is disposed at the distal end of the clipping device 100, and contains the mechanism that converts the proximal and distal movement of the control wire 118 into the actions necessary to deploy and release a hemostatic clip 90. FIGS. 9, 10 and 11 show, respectively, side, top and perspective views of the distal end of the clipping device 100, including the clip assembly 106 having clips in the folded configuration. This configuration is used, for example, to ship the clipping device 100 and to insert the clipping device 100 through the lumen of an endoscope. Some of the components of the clip assembly 106 include a capsule 200 which provides a structural shell for the clip assembly 106, the clip arms 208 which move between open and closed positions, a bushing 202 attached to the distal end of the control wire 118, and a yoke 204 adapted to connect the capsule 200 to the control wire 118.

As depicted, the proximal end of the capsule 200 slides over the distal end of the bushing 202. A locking arrangement between these two components is provided by capsule tabs 212, which lock into the bushing 202 so that mechanical integrity is temporarily maintained between the capsule 200 and the bushing 202. Within the capsule 200 are a yoke 204 and a tension member 206 which transmit forces applied by the control wire 118 to the clip arms 208. The ball 140 formed at the distal end of the control wire 118 is mated to a receiving socket 210 formed at the proximal end of the yoke 204. A male C-section 214 extending from the tension member 206 is received in a corresponding female C-section 216 formed in the yoke 204, so that the two components are releasably connected to one another, as will be described below. The clip arms 208 in the closed configuration have a radius section 300 which is partially contained within the capsule 200 to prevent opening of the arms. Each of the clip arms 208 goes over the tension member 206 and has a proximal end 222 which slips under a yoke overhang 254, to further control movement of the arms 208.

Figure 12:
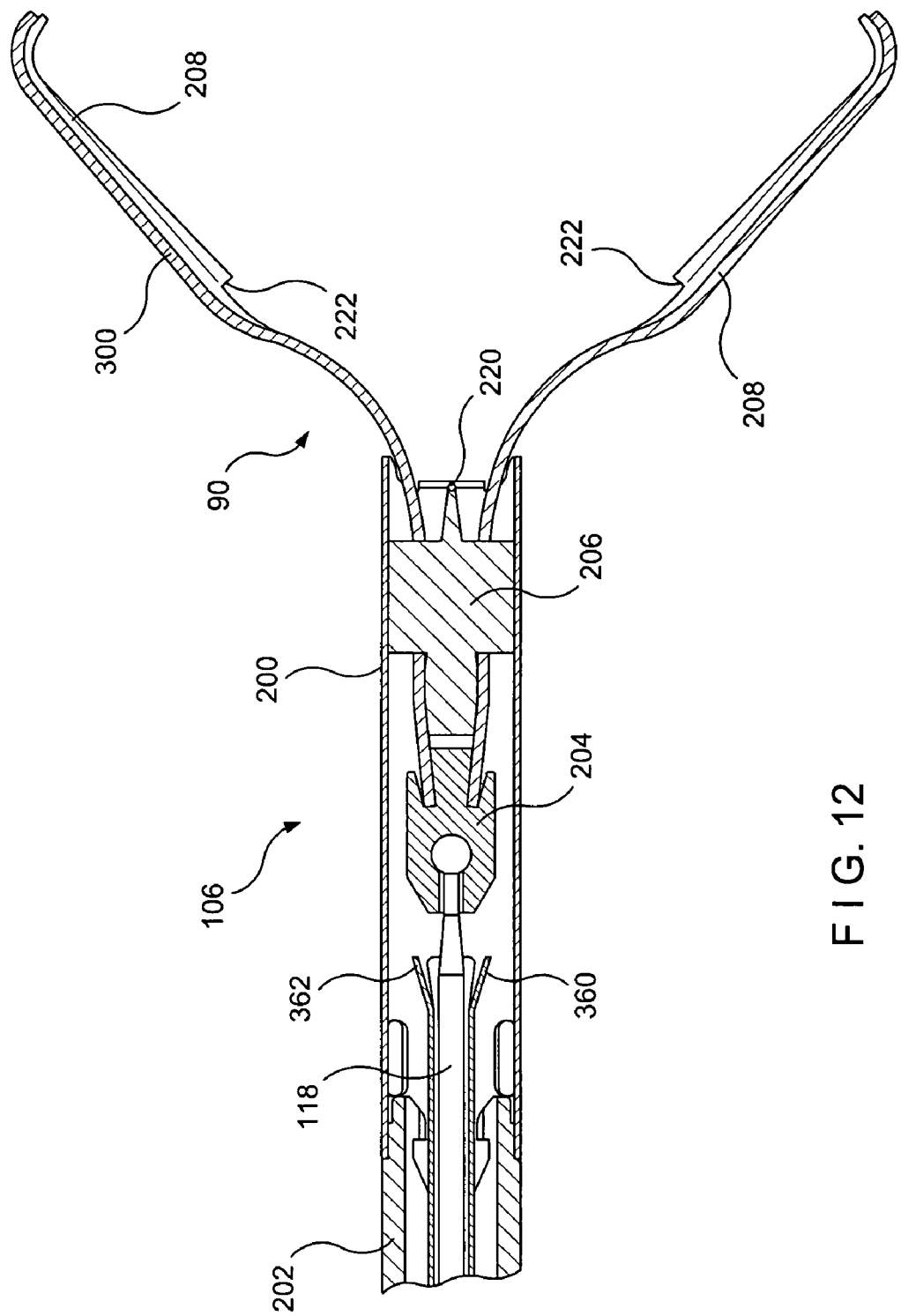
FIG. 12 is a top view of the clip arms according to an embodiment of the present invention.
Figure 13:
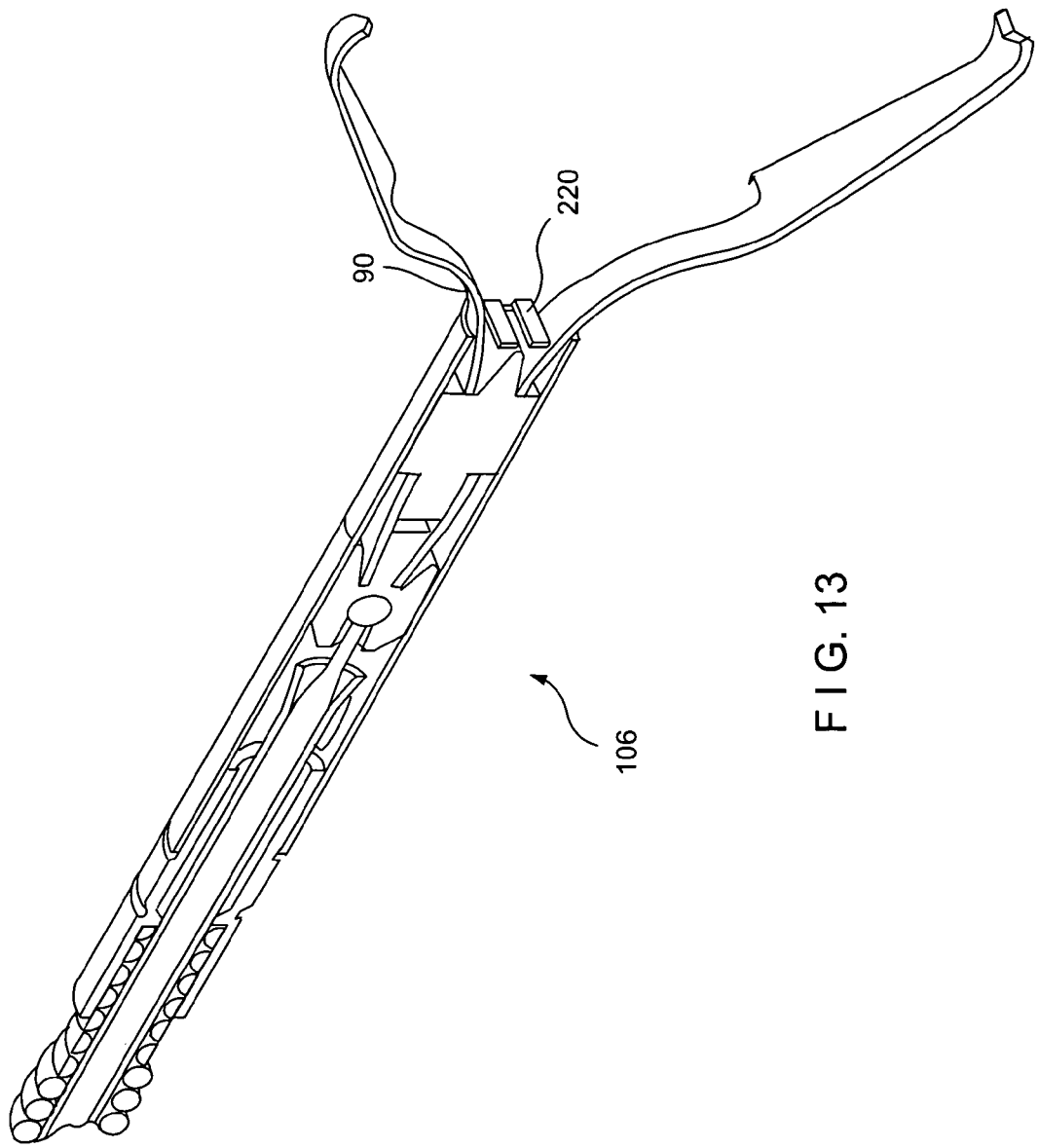
FIG. 13 is a perspective view of the clip arms shown in FIG. 12, according to an embodiment of the present invention.
Figure 15:
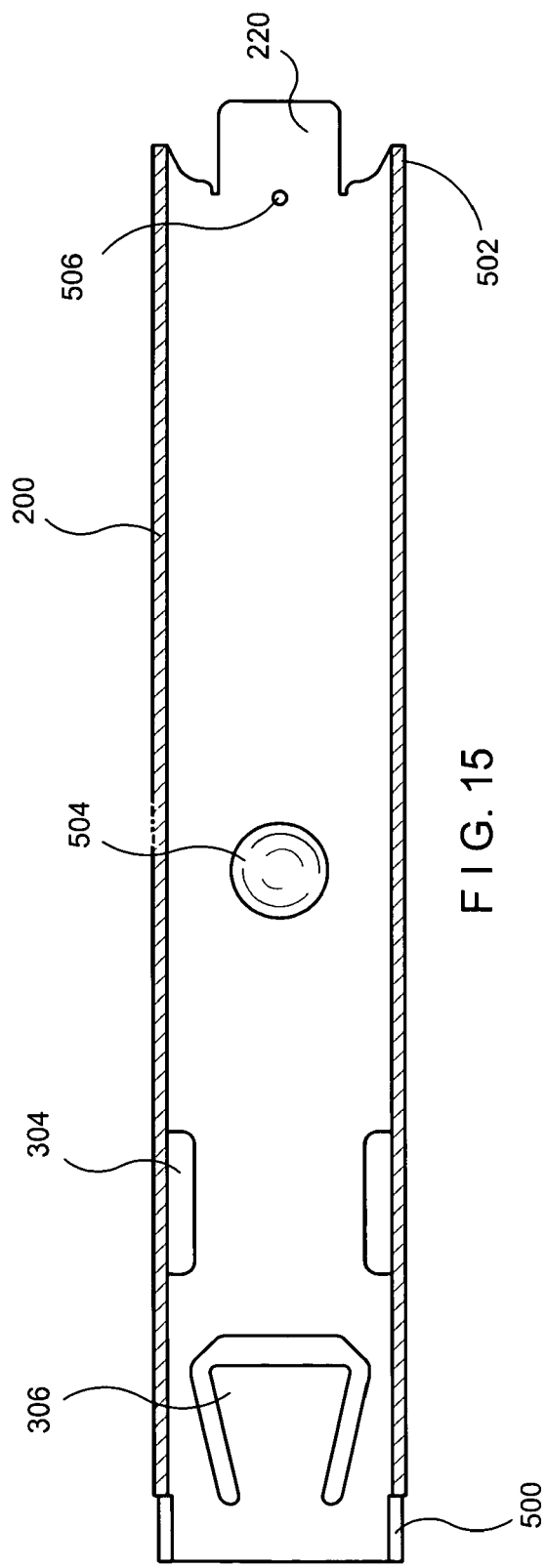
FIG. 15 is a cross sectional side view of the of the capsule shown in FIG. 14.

FIGS. 12 and 13 show, respectively, top and perspective views of one exemplary embodiment of the clip assembly 106 in an open configuration with the clip arms 208 in a fully open position. The open configuration is obtained when the sliding spool 110 shown in FIG. 1 is moved distally so that the ball 140 of the control wire 118 pushes the assembly containing the yoke 204 and the tension member 206 distally, sliding within the capsule 200. As will be described below, the distal ends of the clip arms 208 are biased toward the open position and revert to this position whenever they are not constrained by the capsule 200. In the exemplary embodiment, a maximum opening of the clip arms 208 occurs when the clip arms 208 ride over the folded distal folding tabs 220 which extend from the distal end of the capsule 200, as shown in FIGS. 14 and 15. In this embodiment, the tabs 220 provide a cam surface, and the clip arms 208 act as cam followers, being deflected by the tabs 220. In addition, the folding tabs 220 may also provide a distal stop for the tension member 206, to retain it within the capsule 200. Thus, by moving the sliding spool 110 distally, the user opens the clip arms 208 to prepare to grasp tissue therebetween.

When the sliding spool 110 is moved proximally by the user, the assembly within the capsule 200 also moves proximally and the clip arms 208 are withdrawn within the capsule 200. As the clip arms 208 move proximally within the capsule 200, clip stop shoulders (CSS) 222 contact a distal portion of the capsule 200, for example, the folded tabs 220. This interaction of the CSS 222 with the capsule 200 provides to the user a first tactile feedback in the form of increased resistance to movement of the sliding spool 110. This feedback gives to the operator a positive indication that further movement of the handle control will cause the hemostatic clip 90 to be deployed from the clip assembly 106. The operator may then decide whether the current position of the clip 90 is acceptable or not. If the position is acceptable, the operator can deploy the clip 90 by continuing to move the sliding spool 110 with increased proximal pressure to cause the clip arms 208 to close on the tissue. If not, the operator can move the sliding spool 110 distally to re-open the clip arms 208 and extend them out of the capsule 200, reposition the clip 90, and repeat the above steps to close the clip 90 at a more appropriate location.

When the user determines that the clipping device 100 is positioned correctly, the proximal pressure on the sliding spool 110 may be increased to continue deployment of the hemostatic clip 90 from the clip assembly 106. FIGS. 16 and 17 show respectively a top and side view of the clipping device 100 in this condition. As the proximal tension on sliding spool 110 is increased, the control cable 118 pulls the yoke 204 proximally, away from the tension member 206. The tension member 206 is firmly attached to the clip arms 208 which are prevented from moving proximally by the interaction of the CSS 222 with the folded tabs 220. If sufficient pulling force is applied to the yoke 204, the male C section 214 of the tension member 206 yields and loses integrity with the female C section 216 of the yoke 204. This can occur because, in the exemplary embodiment, the tension member 206 is formed of a material with a lower yield strength than the material of the yoke 204.

The force required to break the tension member 206 away from the yoke 204 may be tailored to achieve a desired feedback that can be perceived by the user. The minimum force required to break the tension member 206 free of the yoke 204 may be selected so that a tactile feedback is felt by the user, to prevent premature deployment of the hemostatic clip 90 while a maximum force may be selected so that other components of the linkage between the sliding spool 110 and the clip arms 208 do not fail before the male C section 214 and the female C section 216 disconnect from one another. In one exemplary embodiment, the tension force necessary to disconnect the two components may be in the range of approximately 4 lbf to about 12 lbf. This range may vary depending on the size of the device and the specific application. To obtain this force at the interface of the male and female C sections 214, 216 a larger force will be applied by the user at the sliding spool 110, since friction within the device may cause losses along the long flexible shaft.

Figure 18:
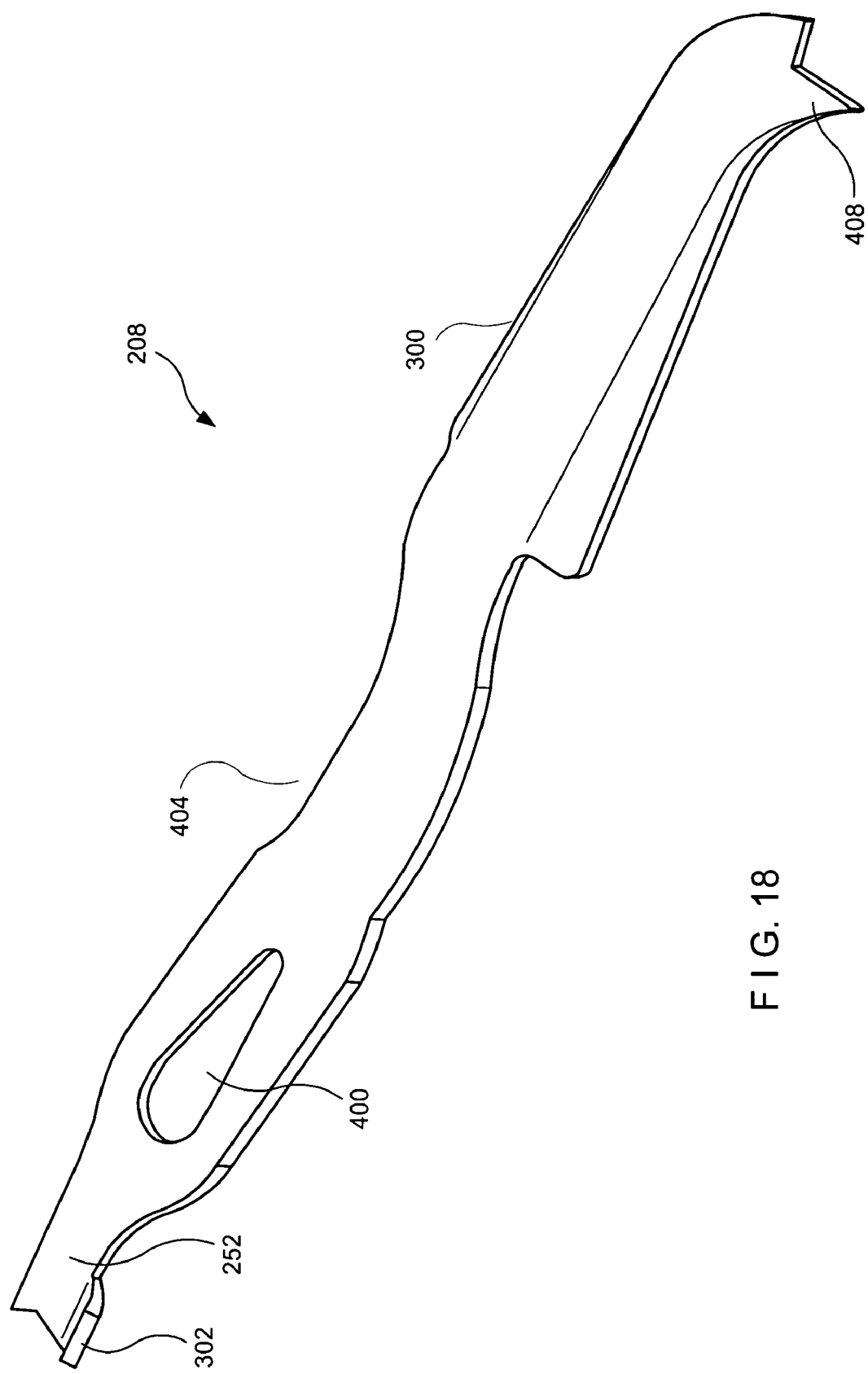
FIG. 18 is a perspective view of a clip arm according to an embodiment of the present invention.

When the male C section 214 of tension member 206 yields, several events take place within the exemplary device 100 nearly simultaneously. More specifically, the yoke 204 is no longer constrained from moving proximally by the CSS 222 abutting the capsule 200. Thus the yoke 204 travels proximally until it comes to rest against a distal bushing shoulder 250. The tension member 206 is not affected by this movement since it is no longer connected to the yoke 204. The proximal ends 252 of the clip arms 208 are normally biased away from a center line of the device 100 and are no longer constrained by the yoke overhangs 254. Accordingly, the clip latches 302 are free to engage the latch windows 304 of the capsule 200, thus maintaining the integrity of the capsule-clip arms combination after deployment. Details of one exemplary embodiment of the capsule 200 are shown in FIGS. 14, 15 and details of the clip arms 208 are shown in FIGS. 18, 19 and 20.

Figure 21:
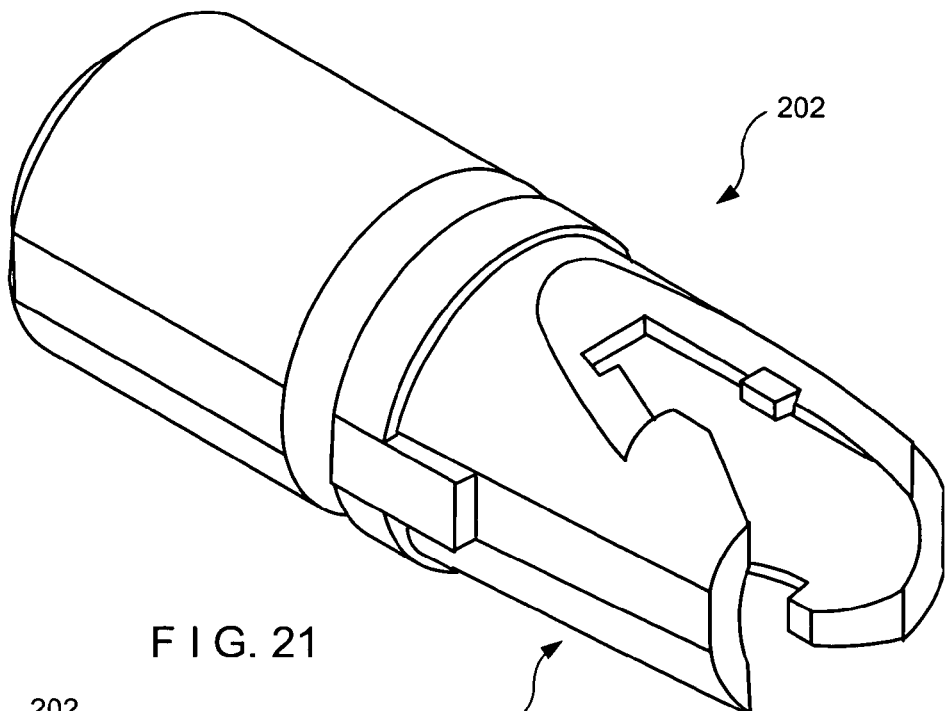
FIG. 21 is a perspective view of a bushing according to an embodiment of the present invention.

As the yoke 204 moves proximally to abut against the bushing 202, the capsule tabs 306 are bent away from the centerline of the capsule 200 by the cam surfaces of the yoke 204. As a result, the capsule tabs 306 are no longer engaged to the corresponding bushing undercuts 350, shown in the side and perspective views of the bushing 202 depicted in FIGS. 21, 22. Since the capsule 200 and the bushing 202 (which is securely connected to shaft section 104) are no longer connected, the clip assembly 106 is prevented from being released from the shaft section 104 only by its connection to the ball 140 of the control wire 118.

Figure 22:
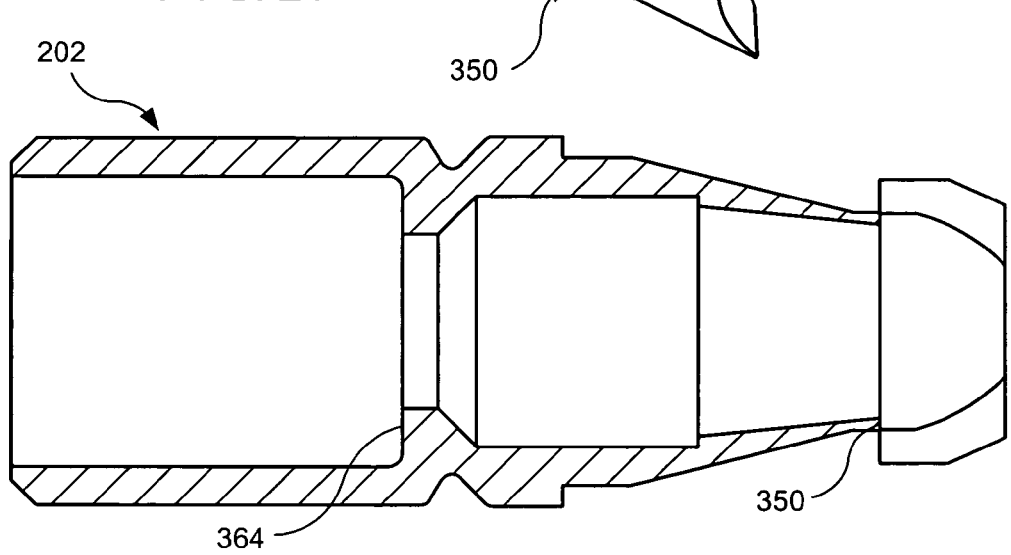
FIG. 22 is a cross sectional side view of the bushing shown in FIG. 21.
Figure 23:
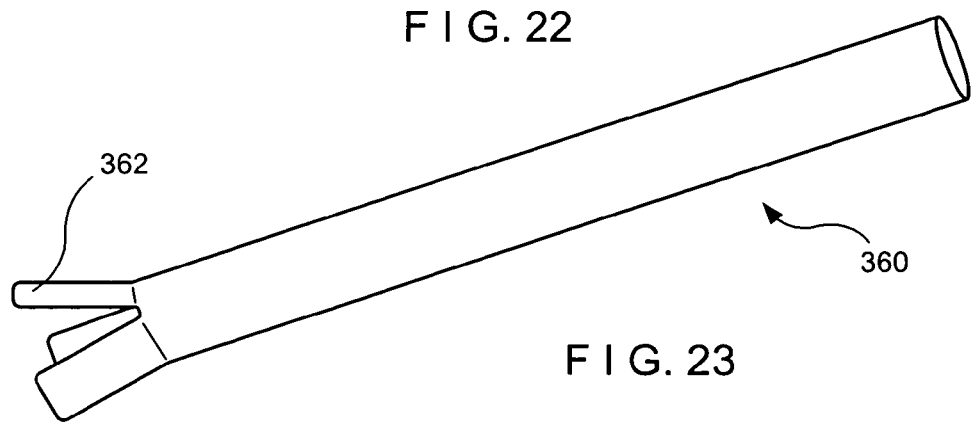
FIG. 23 is a perspective view of a wire stop according to an embodiment of the present invention.

A further result of moving the yoke 204 against the distal bushing shoulder 250 of the bushing 202 is that the distal end of the wire stop 360 (shown in FIGS. 12, 16) is placed near the proximal bushing shoulder 364 (shown in FIG. 22). The flared fingers 362 located at the distal end of the wire stop 360, better shown in FIG. 23, are compressed as they pass through the central ID of the bushing 202, but return to their normally biased open position (shown in FIG. 23) after passing past the proximal bushing shoulder 364. Further distal movement of the sliding spool 110 is thus prevented since that movement would engage the fingers 362 of the wire stop 360 with the proximal bushing shoulder 364. This feature prevents the clip assembly 106 from being pushed away from the bushing 202 before the ball 140 is separated from the control wire 118, as will be described below.

The wire stop 360 comprises a tube with a first slotted and flared end attached to the control wire 118 by conventional means. As shown in FIG. 23, the slots impart flexibility to the device so it can easily pass through the central lumen of the bushing 202. Flared fingers 362 are formed by the slots, and engage the proximal bushing shoulder 364. The wire stop 360 is made of a material that is biocompatible and that has enough resilience so that the fingers 362 re-open after passage through the bushing 202. For example, stainless steel may be used for this application.

One feature of the exemplary embodiment of the invention described above is that the user receives both tactile and auditory feedback as the clip assembly 106 is deployed and released. The separation of the tension member 206 from the yoke 204 produces a small clicking noise and a tactile feel that is perceptible while holding the handle assembly 102. The change in axial position of the sliding spool 110 is thus augmented by the changes in resistance to its movement and by the clicking sound and feel through the start and stop of the movement. As a result the user is always aware of the status of the clip assembly 106, and the inadvertent deployment of a hemostatic clip 90 in an incorrect location is less likely. It will be apparent to those of skill in the art that the order of male and female connectors in the device may be reversed or changed without affecting the operation of the device.

Figure 24:
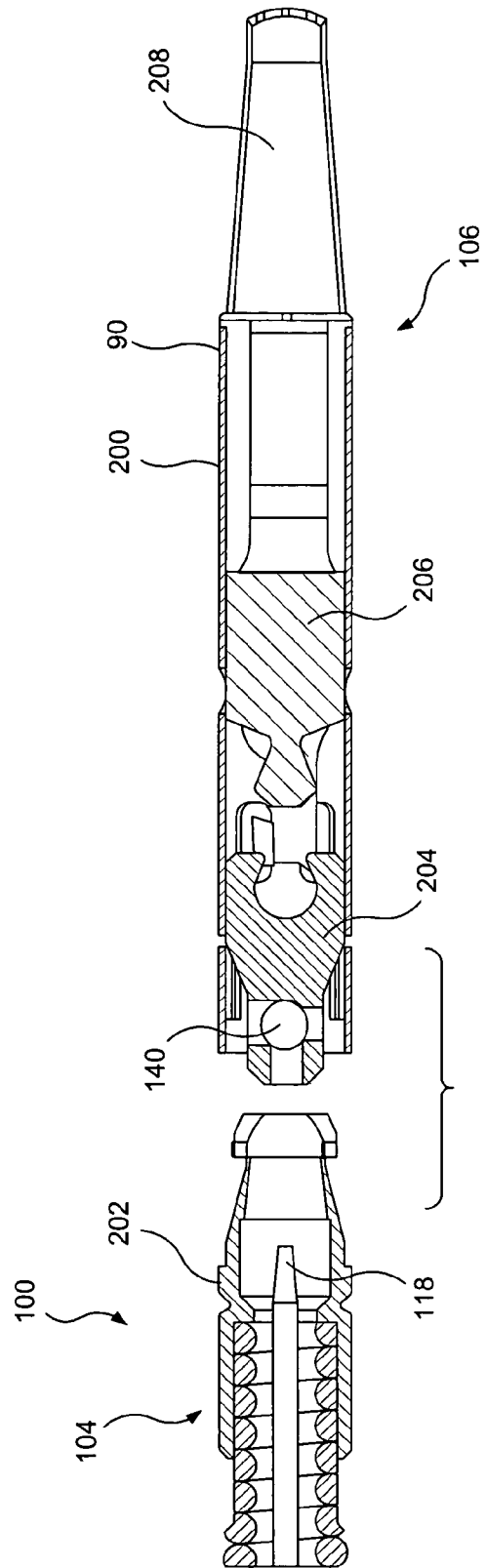
FIG. 24 is a schematic side view of a clip assembly detached from a bushing, according to an embodiment of the present invention.

It may be beneficial for the user to be certain that the clip assembly 106 has been deployed before the rest of the clipping device 100 is removed from the endoscope. Injury to the tissue being treated could result if the clipping device 100 is removed from the operative site while the hemostatic clip 90 is only partially deployed. Accordingly, clear tactile feedback is preferably incorporated, to augment the auditory and tactile feedback stemming from the separation of the yoke 204 from the tension member 206. FIG. 24 depicts the point at which the clip assembly 106 separates from the rest of the clipping device 100. According to the described embodiment, this second user feedback is obtained by designing the control wire 118 so that it will separate from the end ball 140 only when a predetermined tension is applied to it. In other words, the ball 140 of the control wire 118 is mechanically programmed to yield and separate from the body of the control wire 118 when a tension applied thereto reaches a pre-set level. To achieve this, the size of the reduced diameter section 142 may be selected so that, when the user continues to move the sliding spool 110 proximally, this reduced diameter section 142 fails as the programmed yield tension is reached to detach the ball 140 from the tapered section 144. The failure of this reduced diameter section 142 provides an additional and clear tactile feedback to the operator indicating that the clip assembly 106 has been completely deployed.

As the ball 140 detaches, the sliding spool 110 bottoms out at the proximal end of the handle 108, such that a full stroke of the handle assembly 102 is reached. The tension required to cause the reduced diameter section 142 to yield and release the ball 140 may be selected at any desired point within a wide range of values. However, this force will preferably be greater than the tension force required for the male C section member 214 to separate from the yoke 204. If this condition is not satisfied, a situation may occur where the clip assembly 106 is locked in place on the patient's tissue, but cannot be released from the clipping device 100. It will be apparent that this situation should be avoided. In one exemplary embodiment, the tension force required to separate the ball 140 from the body of the control wire 118 is in the range of between about 10 lbf and 20 lbf at the distal end of the control wire 118. As discussed above, losses along the elongated flexible shaft may require the user to apply a force substantially greater than this to the handle body 102.

Once the ball 140 has separated from the rest of the control wire 118, the user may pull the rest of the clipping device 100 from the endoscope. As this is done, the yoke 204 is retained within the capsule 200 by the spring and frictional forces of various features of the capsule 200, such as the capsule tabs 306. Prior to withdrawing the clipping device 100, the over-sheath 150 may be moved distally by the user over the entire remaining portions of the shaft section 104 to prevent damage to the endoscope as the clipping device 100 is withdrawn therethrough. The sheath stop 156 may also be placed on the shaft section 104 proximally of the over-sheath grip 152 to prevent inadvertent sliding of the over-sheath 150 from the distal end of the device 100.

A more detailed description of several components of the clipping device 100 follows. The clip arms 208 are shown in detail in FIGS. 18, 19 and 20; the tension member 206 is shown in side and top views in FIGS. 25, 26; while top and side views of the yoke 204 are shown respectively in FIGS. 27 and 28. The clip arms 208 are preferably formed of a biocompatible material such as Nitinol, Titanium or stainless steel. Maximum spring properties may be obtained by using materials such as 400 series stainless or 17-7 PH. As shown, a tear drop keyway 400 is formed in the clip arm 208 to mate with a corresponding tear drop key 402 formed on the tension member 206. This feature maintains the relative positions of these two components and of the yoke 204 substantially constant. The shape of the keyways 400 may be varied. For example, the keyway 400 may be oval or elliptical. Central portions of the clip arms 208 define a spring section 404. When the proximal ends 252 of the clip arms 208 are under the yoke overhangs 254, the clip arms 208 are allowed to pivot over the tension member 206, which in turn biases the distal ends 252 towards the open configuration so that, when the distal ends of the clip arms 208 are moved distally beyond the distal end of the capsule 200, they move to the open position. In addition, when not restrained by the yoke overhangs 254, the proximal ends 252 of the clip arms 208 spring outward to engage the corresponding latch windows 304 in the capsule 200.

The clip arms 208 also comprise a radius section 300 that adds strength to the clip assembly 106 and reduces system friction. The radius of the radius section 300 preferably approximately matches an inner diameter of the capsule 200 and has a smooth profile to avoid scratching the inner surface of the capsule 200. A pre-load angle α is defined between the radius section 300 and the spring section 404. The pre-load angle α determines how much interference (pre-load) exists between the two opposing clip arms 208 at their distal ends when closed. The greater the pre-load angle α, the greater the engaging force that is applied by the clip arms 208. However, this condition also causes the greatest system friction when the hemostatic clip 90 is closed. The clip arms 208 also comprise interlocking teeth 408 disposed at their distal ends. In the exemplary embodiment, the teeth 408 are identical so that the arms may be interchangeable and will mesh smoothly with the set facing them. The teeth 408 are disposed at a nose angle β which is preferably between approximately 90 and 135 degrees, but in other applications may be greater or lesser than the described range.

One exemplary embodiment of the capsule 200 is shown in detail in FIGS. 14 and 15 and comprises alignment keyways 500 designed to mate with corresponding features on the bushing 202 to rotationally align the two components. The capsule tabs 306 may be bent towards the centerline of the capsule 200 to engage the bushing undercuts 350. The engagement maintains the integrity of the connection between the capsule assembly 200 and the rest of the clipping device 100 until the yoke is pulled into the distal bushing shoulder. The capsule overhangs 502 provide added clamping strength to the deployed clip arms 208. This is achieved by reducing the length of the portion of each clip arm 208 not supported by a portion of the capsule 200. This feature does not affect the amount of tissue that may be captured by the clip arms 208 since the capsule overhangs 502 extend on a plane substantially parallel to the plane of the clip arms 208.

Additional features of the capsule 200 include an assembly aid port which may be used to assist in aligning the components of the clip assembly 106. Bending aids 506 facilitate a smooth bend when the distal folding tabs 220 are bent inward, as described above. The bending aids 506, as shown, are holes aligned with the folding line of the tabs 220, but may also include a crease, a linear indentation, or other type of stress concentrator. The capsule 200 may be formed from any of a variety of biocompatible materials. For example, stainless steel, Titanium or Nitinol or any combination thereof may be used. High strength polymers like PEEK™ or Ultem™ may also be used to form the capsule 200, with a heat set treatment being used to adjust positionable elements.

Figure 26:
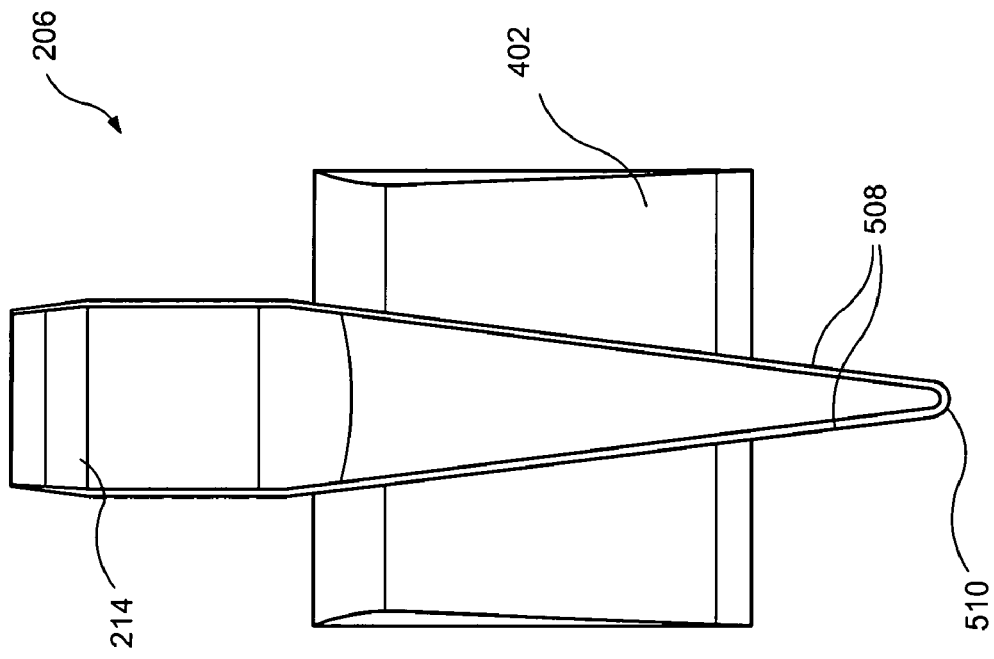
FIG. 26 is a top view of the tension member shown in FIG. 25.
Figure 25:
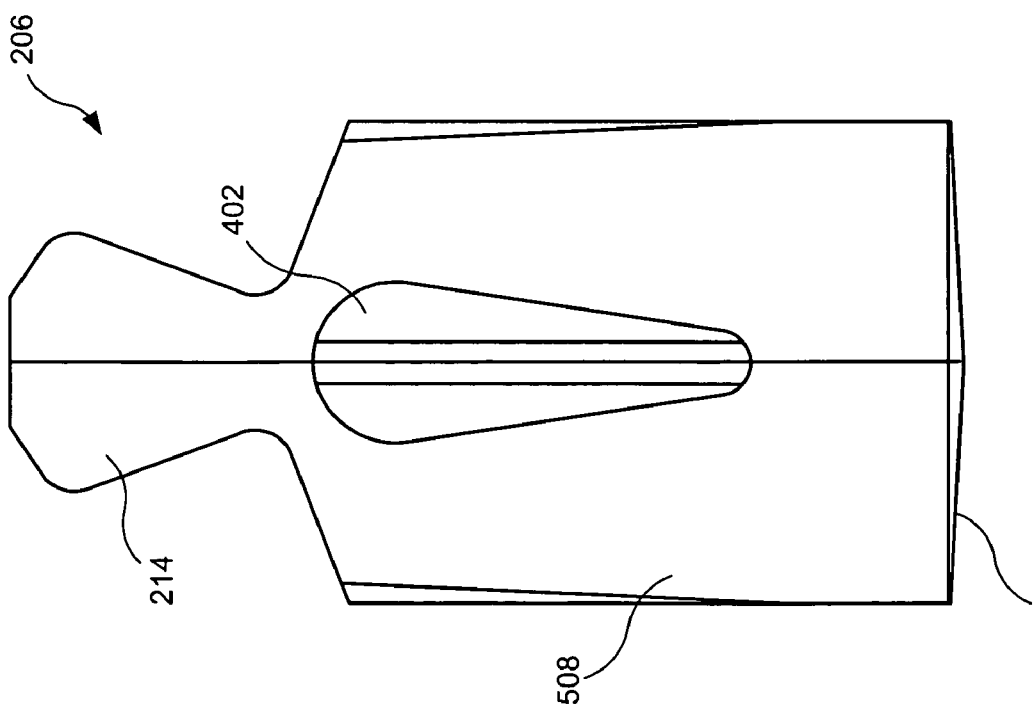
FIG. 25 is a side view of a tension member according to an embodiment of the present invention.

FIGS. 25 and 26 depict additional details of the tension member 206. As shown, tear drop keys 402 are designed to engage the tear drop keyways 400 of the clip arms 208, as described above. Clip follower planes 508 are shaped to form a fulcrum which allows the clip arms 208 to rock between the open and closed configurations. The tension member 206 comprises a distal stop face 510 which abuts the distal folding tabs 220 of the capsule 200 to stop the distal motion of the capsule assembly 106. In general, all surfaces and edges of the tension member 206 that are in contact with the inner surfaces of the capsule 200 preferably have a radius substantially similar to an inner radius of the capsule 200 to provide a sliding fit therein. The tension member 206 is preferably formed of a biocompatible polymer, monomer or thermoset. The type of mechanism selected to release the tension member 206 from the yoke 204 may determine the type of material used since a release due to fracture of the male C section 214 requires a relatively brittle material while release due to yielding without fracture calls for a softer material.

Figure 27:
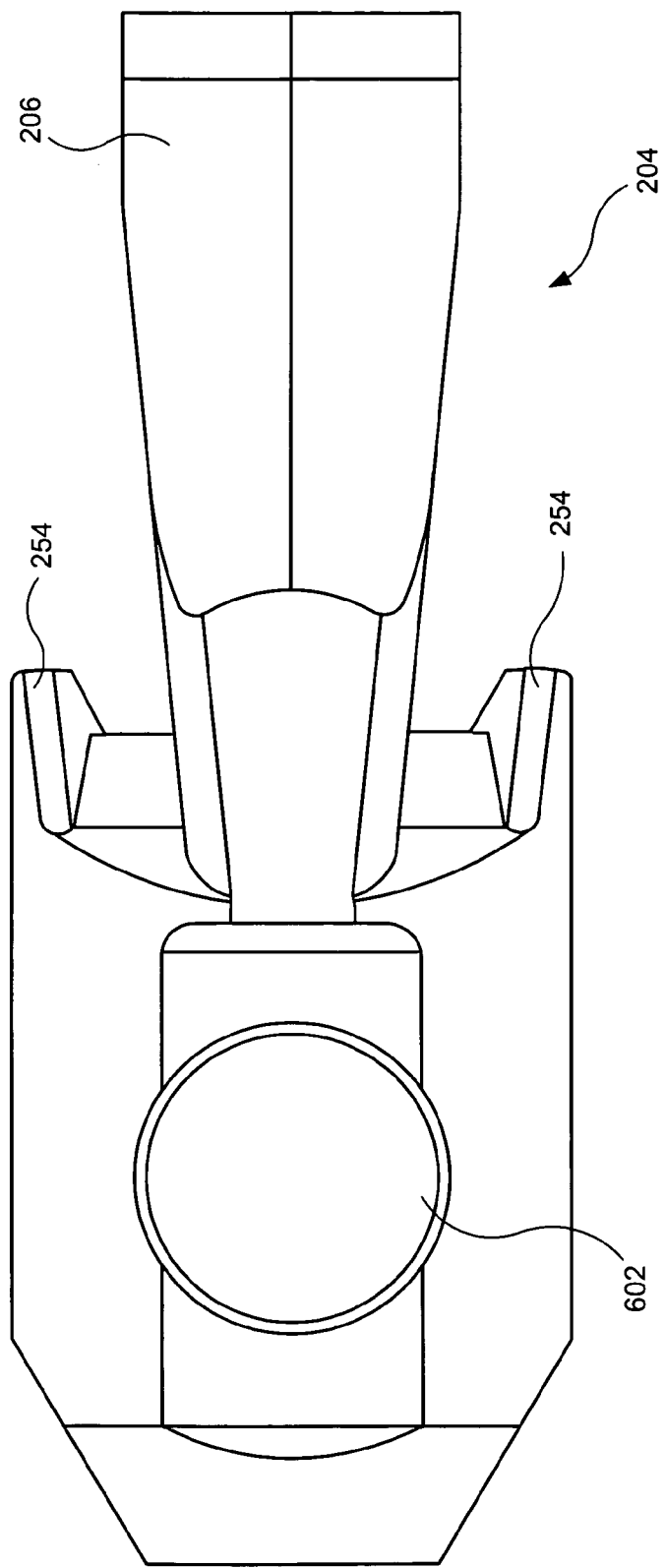
FIG. 27 is a top view of a yoke according to an embodiment of the present invention.
Figure 28:
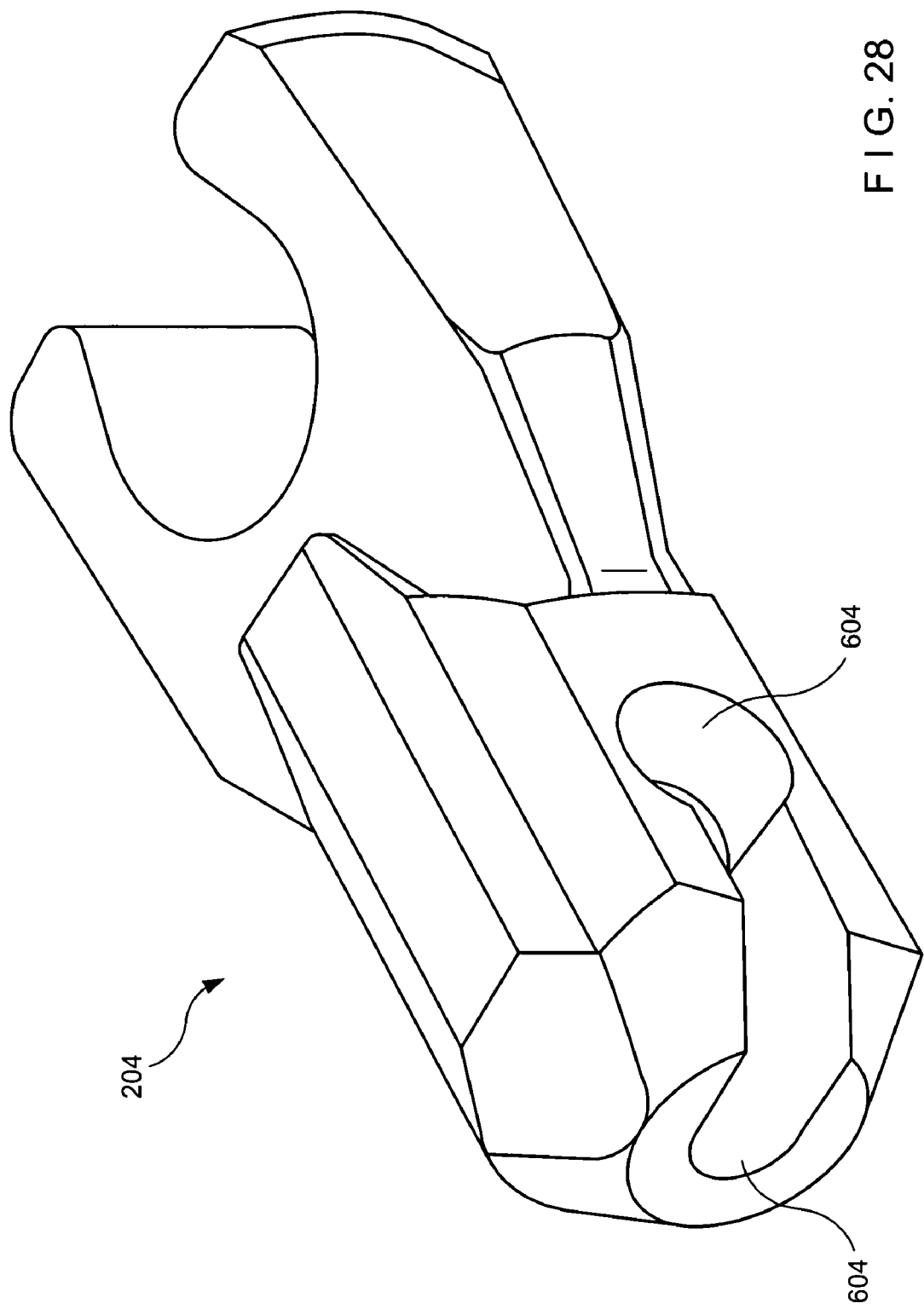
FIG. 28 is a perspective view of the yoke shown in FIG. 27.
Figure 29:
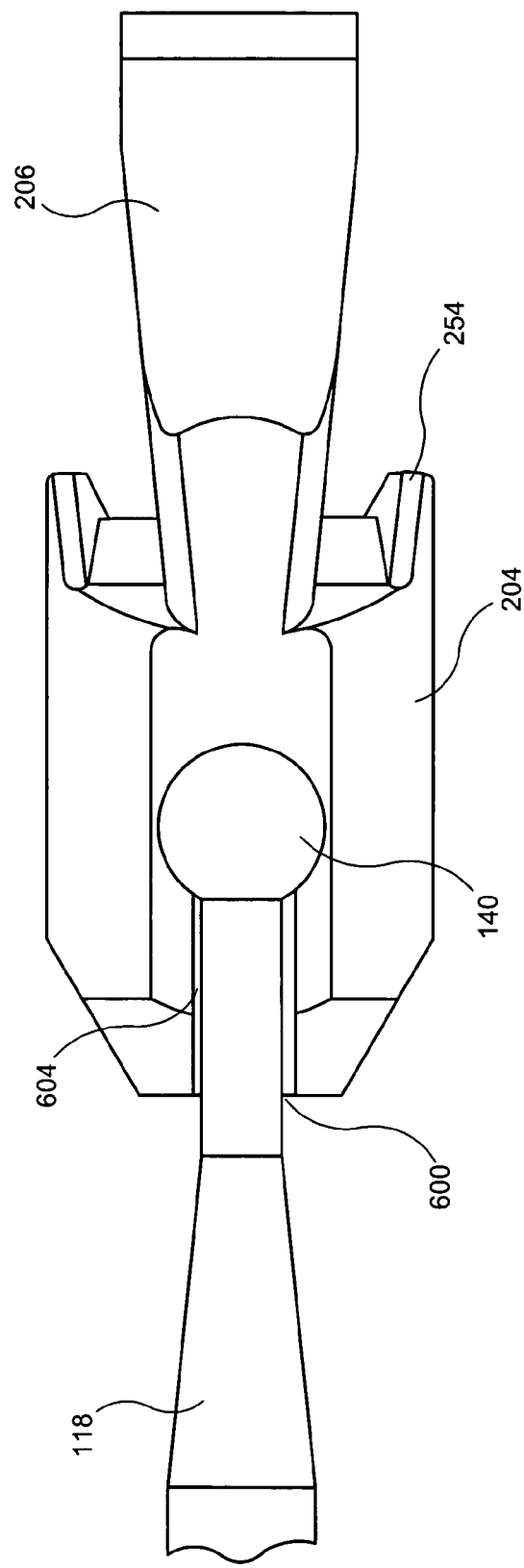
FIG. 29 is a top view of a yoke with a control wire according to an embodiment of the present invention.

Additional details of the yoke 204 are shown in FIGS. 27-29. When the control wire 118 is seated in the yoke 204, it is desirable to prevent inadvertent removal of the control wire 118 from the control wire slot 600. Accordingly, in the present embodiment the ball cavity 602 has a diameter sufficiently large to allow the ball 140 to pass therethrough while the wire cavity 604 is large enough to allow the control wire 118 to pass therethrough, but not large enough to allow the ball 140 pass therethrough. To assemble the control wire 118 with the yoke 204 according to the exemplary embodiment, the proximal end of wire 140 is inserted into the ball cavity 602 until the ball bottoms out, and then the control wire 118 is rotated until it is seated in the control wire cavity 604. This constrains further movement of the ball 140. According to the present embodiment, the yoke 204 is preferably made of a biocompatible metal such as stainless steel or a high strength polymer such as Ultem™.

According to embodiments of the present invention, the clipping device 100 may be scaled to fit the requirements of different surgical procedures. In one exemplary embodiment, the clipping device 100 is sized to fit through an endoscope having a working channel diameter of approximately 0.110 inches. The exemplary bushing has a length of about 0.22 inches and an OD of approximately 0.085 inches. The exemplary capsule 200 has a length of about 0.5 inches, an OD of about 0.085 inches, and a wall thickness of about 0.003 inches. When assembled, the rigid length of the exemplary capsule 200 and the bushing 202 is approximately 0.625 inches. It is important to maintain this length short enough so that the assembly will not have difficulty passing through bends of the flexible endoscope. In the exemplary clipping device, the outer sheath has an ID of approximately 0.088 inches and an OD of about 0.102 inches. The overall length of the exemplary clipping device is approximately 160 inches, while the tissue grasping portion of the clip arms 208 is approximately 0.4 inches long.

When treating internal bleeding and, in particular, when treating gastrointestinal bleeding, it is often necessary to apply more than one hemostatic clip. Conventional treatment methods involve repeatedly utilizations of single clip deployment apparatus. With these devices, either a new device has to be inserted to the target site for each new clip to be applied or the same device must be removed and reloaded with a clip before being reinserted to the target site. After insertion through the endoscope to the target site, the device has to be re-positioned over the target site tissue before the new clip may be deployed.

In a further embodiment of the present invention, a multiclip endoscopic hemostatic device may be used to discharge multiple hemostatic clips without removing the device from the endoscope. This multiclip device achieves equal or better results than conventional single deployment clipping devices, while greatly facilitating the placement of multiple hemostatic clips. In one embodiment, the clips used by the multiclip device according to the present invention are substantially similar in size to conventional hemostatic clips, and thus can be used with conventional endoscopes. According to the invention, the cost of manufacturing the multiclip apparatus is sufficiently low to permit the units to be disposable after use on a single patient.

According to the invention, the multiclip hemostatic clipping apparatus is used in a minimally invasive environment, such that it is applied to the surgical site through an endoscope. The distal end of the hemostatic multiclip device is inserted through the working lumen of the endoscope, and is brought in the vicinity of the surgical site where the bleeding occurs. For example, an endoscope having a working channel of about 1.8 mm inner diameter or greater may be used to reach the surgical site. The proximal ends of the endoscope and of the hemostatic multiclip device are provided with hand controls used by the user/physician to operate the devices.

The hemostatic multiclip device according to an exemplary embodiment of the present invention uses a magazine containing a plurality of hemostatic clips that is advanced through the endoscope's working lumen, to a location near the surgical site. The magazine may be attached to a sheath which protects the inner surfaces of the endoscope from damage caused by, for example, contact with sharp edges of the magazine and clip assembly, and which extends beyond the magazine through the length of the endoscope. The hemostatic clips are joined in a clip chain which is inserted in the magazine and is free to translate in the magazine within certain limits as will be described below. Each of the clips may be formed, for example, of sheet metal or of another material having appropriate mechanical and bio-compatibility properties. The material of the clips is selected to resist plastic deformation while constrained in the closed configuration, so that the hemostatic clips will return to the open configuration when not otherwise restrained.

A modified version of the clipping device 100, shown in FIGS. 1 and 2, may be used with the clip magazine and clip chain described above. A clip magazine containing multiple hemostatic clips may be inserted into the proximal end of the shaft section 104, such that the clips are deployed from the distal end thereof. A handle 108 and sliding spool 110, or similar implements, may be used in conjunction with a control linkage to operate the multiclip dispensing apparatus, as will be described in detail below.

Figure 31:
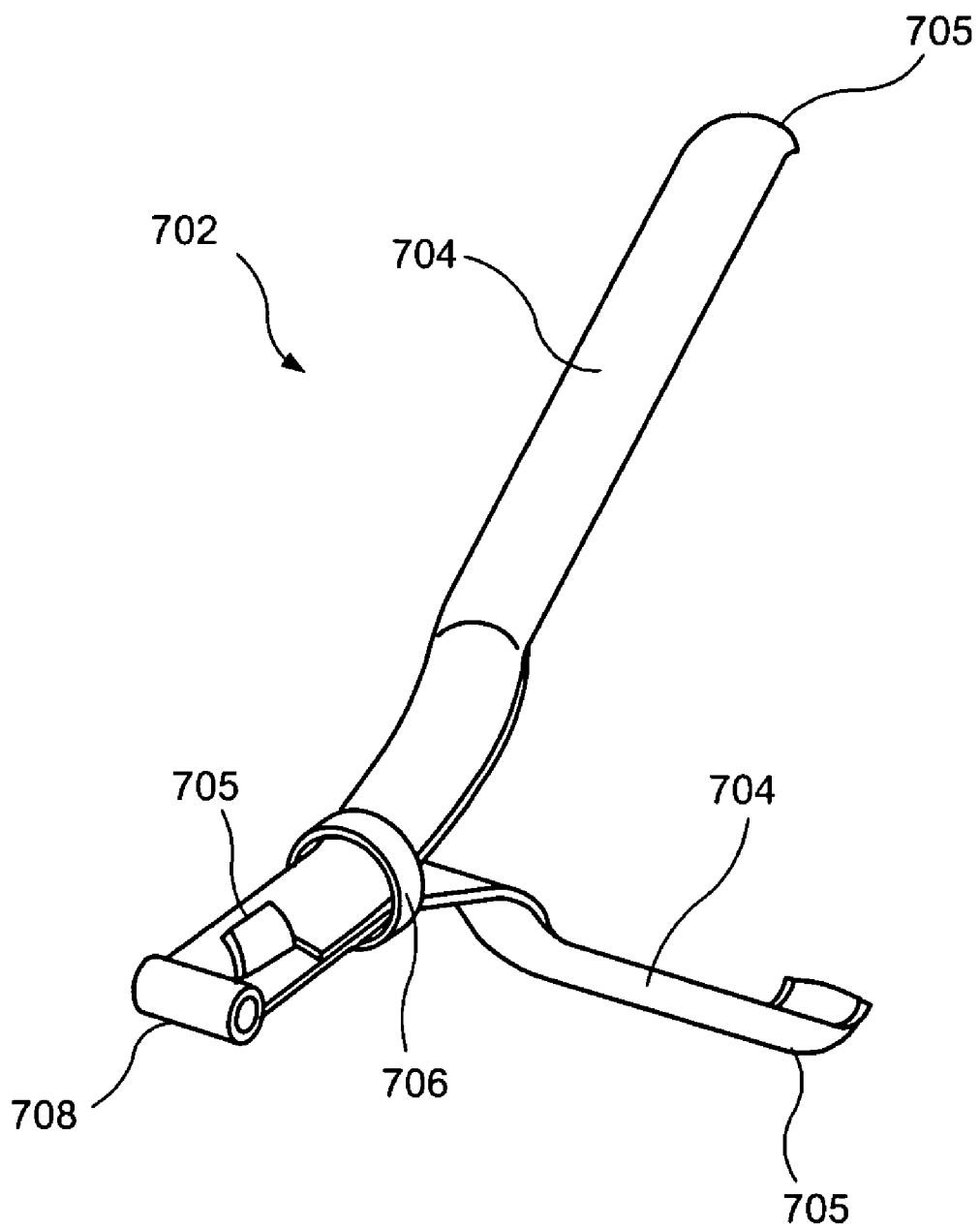
FIG. 31 shows a perspective view of an individual hemostatic clip of a clip chain according to an embodiment of the invention.

FIG. 31 shows an exemplary embodiment of a hemostatic clip according to the present invention. An exemplary clip 702 comprises two clip arms 704 which have inner surfaces facing one another for grasping and retaining tissue therebetween when placed in a closed configuration. FIG. 31 shows the clip arms 704 in an open configuration assumed by the clip 702 in an early phase of deployment, before the tissue is clamped thereby. The clip 702 may be formed of two parts joined at a common portion 705, or may be of a single piece construction. In the exemplary embodiment, the clip 702 is biased toward the open configuration as shown in FIG. 31. A sliding lock ring 706 is used to lock the clip arms 704 in the closed configuration assumed by the clip 702 as it is clamped on tissue.

In different exemplary embodiments, the sliding locking ring 706 may be replaced by different devices adapted to lock the clip arms 704 in the closed configuration. For example, as shown in FIG. 33, a plurality of protrusions with catches 710 may be formed on each of the clip arms 704' of the clip 703 to retain the device in the closed configuration once the clip 703 has been clamped in place on tissue. FIG. 34 shows another exemplary embodiment of a locking mechanism for the hemostatic clip 705 in which a single snap 712 extends from each of the clip arms 704" to lock with a corresponding snap 712 extending from an opposing clip arm 704". The specific mechanism used to lock the clip arms 704 in the closed configuration may be selected depending, for example, on the desired size of the device and on the strength of the desired clamping force. In addition, a distal portion of the magazine containing the clip chain may be shaped to close the clip arms 704', 704" so that the snaps 710, 712 lock in the closed configuration.

As indicated above, a plurality of clips may be loaded in the magazine for use with the hemostatic multiclip device according to the present invention. FIG. 32 shows an exemplary embodiment of a clip chain 700 according to the invention. The clip chain 700 is formed by joining hemostatic clips 702 to one another head to tail using, for example, a linking feature 708. The linking feature 708 comprises an attachment which binds two adjacent clips 702 to one another for so long as there is no movement of the joined clip ends in a direction perpendicular to a longitudinal axis of the clips. In this manner, the clip chain 700 remains intact as long as the clips are translated in a direction generally along the longitudinal axis of the clips. A clip 702 is released from the adjacent clip 702 by moving the joined ends of the clips 702 relative to one another in a direction perpendicular to the longitudinal axis of the clip chain 700. For example, the linking feature lining feature 708 is clamped between distal ends of clip arms 704 which are held in the closed configuration. The linking feature 708 may be formed integrally with the body of hemostatic clip 702, or may be an optional addition that may be attached to more conventional clips.

Figure 35:
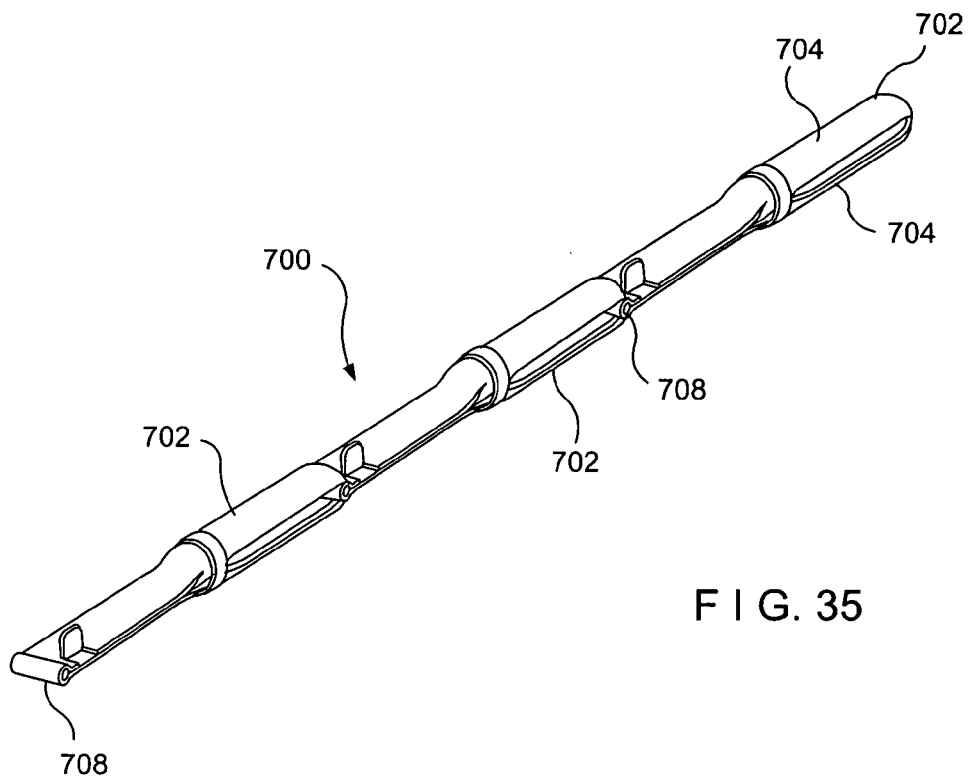
FIG. 35 shows a perspective view of the clip chain shown in FIG. 32.
Figure 36:
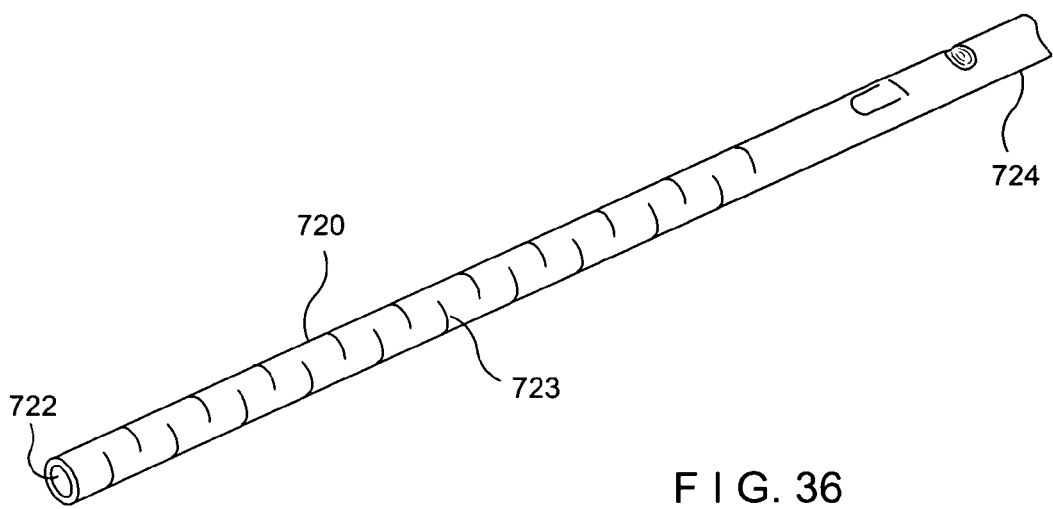
FIG. 36 shows a perspective view of a clip magazine according to an embodiment of the invention.

An exemplary clip magazine 720 is shown in perspective view in FIG. 36. The clip chain 700 (shown in perspective view in FIG. 35) is inserted longitudinally into a hollow channel 722 of the magazine 720, as shown in FIG. 38. The magazine 720 according to this embodiment is a generally cylindrical structure located at the distal end of the hemostatic multiclip device, which contains a portion or all of the clips 702 within the clip chain 700. The magazine 720, together with the clip chain 700, forms a capsule having dimensions and sufficient flexibility to comply with the curvature of the endoscope's working channel. Optional compliance features 723 are included to impart flexibility to the body of the magazine 720 and may, for example, comprise a plurality of partially circumferential slits formed in the magazine 720.

The most proximal of the clips 702 is releasably connected to a control link 726. The control link 726 carries compression and tension loads, so that clip chain 700 may be translated in both directions through forces transmitted via the control link 726. The control link 726 according to the exemplary embodiment of the invention may be formed, for example, as a rigid tube, a semi rigid wire, or by any other structural element capable of transmitting tension and compression loads along the length of the hemostatic multiclip device. The control link 726 is connected to a control handle at the proximal end, to give to the surgeon control of the deployment of the clips 702.

Figure 30:
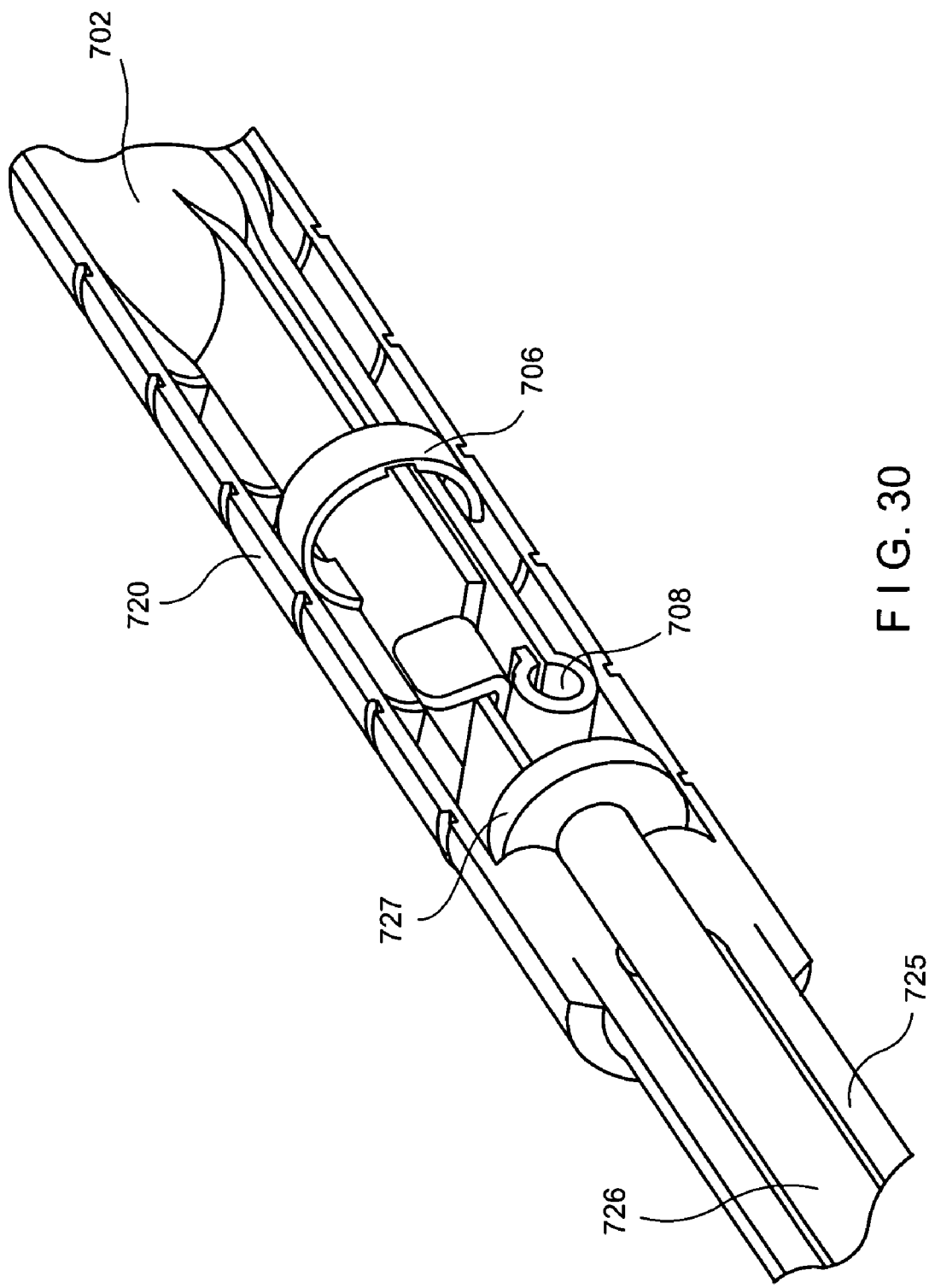
FIG. 30 shows a detail of a connection between a control link and a clip chain according to an embodiment of the invention.

FIG. 30 shows a detail of the connection between the control link 726 and the most proximal hemostatic clip 702. In this embodiment, the control link 726 is formed as a rod or tube which terminates in a connector portion 727 adapted to push against the lining feature 708. A connector portion 727 may also be designed to apply a tension force to the lining feature 708, in a known manner. An optional sheath 725 is used to encapsulate the control link 726, to protect the working channel of the endoscope from damage and to reduce friction between the moving control link 726 and the clip magazine 720.

A control handle portion of the hemostatic multiclip device (not shown) is provided at the proximal end of the device, extending outside of the proximal end of the endoscope to form a clip deployment control element. The control portion may be similar to that shown in FIG. 1 comprising hand controls which operate the control link 726 to cause the deployment and release of successive clips 702. For example, hand movements of the surgeon may be transformed within the control portion into longitudinal movements of the control link 726 along the working channel of the endoscope. In an exemplary embodiment, the clip chain 700 is rigid in compression and supports tensile loads, at least while contained within the clip magazine 720. The clip chain 700 can therefore be translated along the magazine 720 via movement of the control link 726.

As shown in FIG. 38, the clip chain 700 is formed of a plurality of hemostatic clips 702 which remain attached to one another while they are within the cylindrical containment of the clip magazine 720 which supports and constrains the clips 702 of the clip chain 700 in the radial direction through a large portion of its length. This prevents pairs of adjacent clips 702 from disconnecting from one another by preventing relative radial movement between the clips 702. In particular, the radial movement of the substantially closed clip arms 704 of a first hemostatic clip is prevented, so that the linking feature 708 of a second clip, adjacent to the first clip, is not released. The exemplary clip chain 700 minimizes the width of the device, as the clip chain 700 is no wider than the clips 702 themselves.

The diameter of the clip chain 700 works in conjunction with the shape of the distal end 724 of the clip magazine 720 to control the position of the distal portion of the clip chain 700 therethrough. As shown in FIG. 37, the magazine 720 has a reduced cross-section portion 730 limiting the diameter of items passing therethrough. Specifically, the reduced cross-section portion 730 is sized to allow passage therethrough of only a single clip 702 unattached to another clip at its distal end. The diameter of two connected clips 702 is slightly greater than the diameter of a single, unattached clip 702 as the clip arms 704 are not fully closed when they are locked onto the linking feature 708 of another clip 702. Thus, in the exemplary embodiment, an inner diameter of the reduced cross-section portion 730 is selected to be slightly greater than the outer diameter of a single, unattached clip 702 and slightly less than the outer diameter of a clip 702 which is attached to an adjacent clip 702.

The function of the clip chain 700 is better shown in FIGS. 39, 40, where a clip 702' is placed to lead the clip chain 700 through the distal end 724 and through the reduced cross-section portion 730. As the control element 726 is pushed distally in a distal stroke, the clip chain 700 is pushed distally until further distal movement of a next most distal clip 702 coupled to the proximal end of the most distal clip 702 is stopped by the reduced cross-section portion 730. In this position, the most distal clip 702' extends out of the magazine 720 with the clip arms 704 moved to the open position by their bias. Those skilled in the art will understand that other mechanisms (e.g., a camming mechanism) may be employed to ensure that the clip arms 704 move to the open configuration when the clip 702 is pushed distally from the magazine 720.

Figures 41, 42:
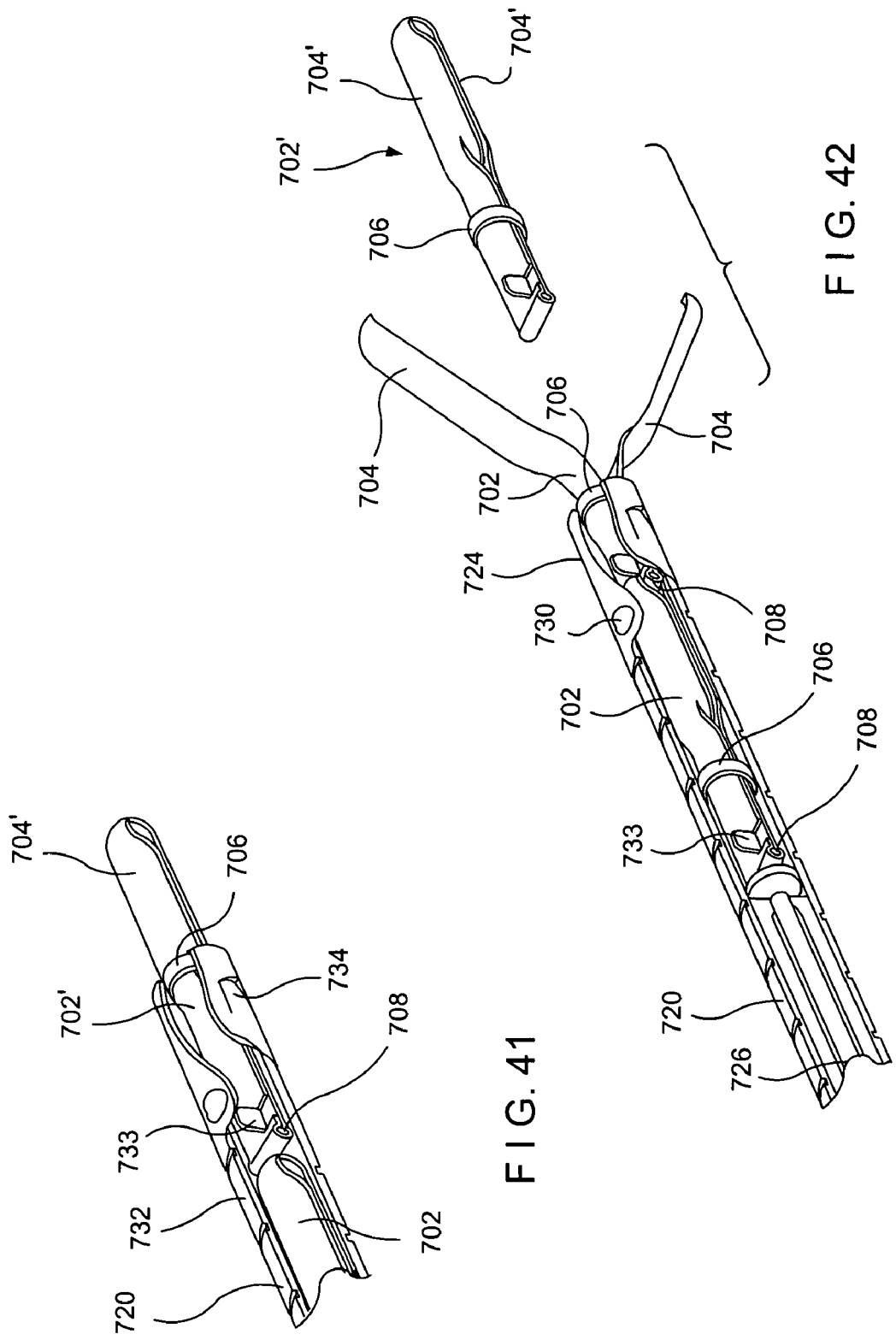
FIG. 41 shows a distal end detail of the clip magazine shown in FIG. 39.
FIG. 42 shows the clip chain of FIG. 38 with a clip deployed and released from the clip chain.

FIG. 39 shows a configuration wherein the most distal hemostatic clip 702' has been pushed distally out of the clip magazine 720, past the distal end 724 thereof. As the control link 726 continues to push distally during the distal stroke, the clip arms 704 of the next most distal clip 702 of the chain 700 abut the reduced cross-section portion 730 (FIG. 40). Once the user has placed the open most distal clip 702' over the desired portion of tissue, the control link 726 is pulled proximally in a proximal stroke, so that the clip chain 700 (including the most distal clip 702') is pulled proximally into the magazine 720, as shown in FIG. 41. The clip sliding lock ring 706 is held distally by lock ring anti-pull back tabs 734 as the most distal clip 702' is pulled proximally. This causes the lock ring 706 to move partially over the clip arms 704' locking them in the closed configuration and firmly grasping therewithin. At this point the most distal clip 702' is clamped securely over the tissue, but is still attached to the clip chain 700 via the linking feature 708.

After deployment and clamping of the most distal clip 702' has been achieved, further proximal movement of the control linkage 726 during the proximal stroke causes separation of clip 702' from the clip chain 700. Additional features may be formed on the clip 702' or on the lock ring 706 to cooperate with the distal end 724 and prevent further proximal movement of the distal clip 702' relative to the magazine 720. The pull back distance of the most distal clip 702' may be controlled, for example by selecting a position of the additional feature 733 so that the link between the most distal clip 702' and the next most distal clip 702 is located in a relief portion 732 of the distal end 724. The relief portion 732 includes a movable tab or opening which allows local diametrical expansion of a clip 702 within that portion of the magazine 720.

As continued proximal tension force is applied by the control link 726 during the proximal stroke of the control link 726, the clip arms 704 of the next most distal clip 702 are pushed diametrically outward over the linking feature 708 of the most distal hemostatic clip 702', which now acts as a cam surface. The relief portion 732 of the clip magazine 720 allows outward expansion of the clip arms 704 over the linking feature 708 to permit the clip arms 704 to continue moving proximally and separate from the most distal clip 702'. The distal most clip 702' is still prevented from moving further proximally by the additional feature 733 described above, but is now free to move distally and exit the magazine 720.

The most distal clip 702', after release from clip chain 700, exits the clip magazine 720 due to the tension applied to it by the tissue clamped thereby. Alternatively, the clip 702' may be pushed out of the magazine 720 by distal movement of the clip chain 700 as the next most distal clip 702 is pushed toward the distal end 724. FIG. 42 depicts a configuration in which the "former" most distal clip 702' has been ejected from the clip magazine 720, and is clamped securely to the target tissue. A "new" most distal clip 702 is now positioned partially out of the magazine 720 with its clip arms 704 in the open configuration. The "new" most distal clip 702 is still connected to the clip 702 immediately proximal to it which is positioned fully inside of the clip magazine 720 and which forms part of the clip chain 700. At this point, the user may position the open clip arms 704 over a new portion of desired tissue and repeat the process described above to clamp the clip arms 704 over the tissue, lock them closed, and release the new distal-most clip 702 from the clip chain 700 and eject the clip 702 from the clip magazine 720.

The present invention has been described with reference to specific exemplary embodiments. Those skilled in the art will understand that changes may be made in details, particularly in matters of shape, size, material and arrangement of parts without departing from the teaching of the invention. For example, different shapes of the clip chain and clip magazine may be employed. Accordingly, various modifications and changes may be made to the embodiments without departing from the broadest scope of the invention. The specifications and drawings are, therefore, to be regarded in an illustrative rather than a restrictive sense.

What is claimed is:

1. An apparatus for applying clips to tissue, comprising:
a plurality of clips linked to one another to form a clip chain;
a control linkage coupled to a proximal-most one of the clips for applying tension and compression to the clip chain; and
a magazine containing the clip chain, the magazine including an abutment surface sized to permit passage distally therebeyond only of a distal-most clip of the clip chain, the clips being biased so that, when a distal-most one of the clips is moved distally out of the magazine, arms of the distal-most clip move apart to a tissue receiving configuration, a distal opening of the magazine being shaped so that, as the distal-most clip is drawn back into the opening through the application of tension to a proximal-most clip of the clip chain, the clip arms of the distal-most clip are drawn together to grip tissue received therebetween.

2. An apparatus for applying clips to tissue, comprising:
a plurality of clips, each of the clips including a distal end having a pair of opposed jaws and a proximal end including a linking feature, where the clips are linked to one another to form a clip chain with a linking feature of a distal-most one of the clips being gripped between the jaws of an immediately proximal one of the clips;
a control linkage coupled to a proximal-most one of the clips for applying tension and compression to the clip chain; and
a magazine containing the clip chain, the magazine including an abutment surface sized to prevent passage distally therebeyond of a clip having received between its jaws a linking feature of an immediately distal clip and an opening location within which the jaws of a clip are permitted to open to release a linking feature therefrom, the clips being biased so that, when a distal-most one of the clips is moved distally out of the magazine, arms of the distal-most clip move apart to a tissue receiving configuration, a distal opening of the magazine being shaped so that, as the distal-most clip is drawn back into the opening through the application of tension to a proximal-most clip of the clip chain, the clip arms of the distal-most clip are drawn together to grip tissue received therebetween.

3. The apparatus according to claim 2, wherein the magazine further comprises a closing element closing and locking distal-most clip when the distal-most clip is withdrawn proximally into the magazine after having been moved distally out of the magazine to grip tissue between its jaws.

4. The apparatus according to claim 3, wherein the closing element comprises anti-pull back tabs positioning a lock ring over the jaws of the distal-most clip.

5. The apparatus according to claim 3, wherein the closing element is formed at a distal end of the magazine as an inward projection shaped to close snaps on the jaws of the distal-most clip.

6. The apparatus according to claim 2, wherein the opening location comprises one of a flexible tab movable radially outward, an opening in a wall of the magazine, an increased inner diameter section of the magazine wall and a radially expandable section of the magazine wall.

7. The apparatus according to claim 1, wherein the jaws of the clips are biased toward an open configuration.

8. An apparatus for applying clips to tissue within a body, comprising:
an elongate body extending from a proximal end which, when in an operative position, remains outside the body to a distal end which, when in the operative position extends into the body to a location adjacent to a target portion of tissue to which one or more clips are to be applied;
a control element extending through the elongate body to the distal end thereof; and
a magazine formed at the distal end of the elongate body, the magazine housing therein a chain of clips with a proximal-most one of the clips being coupled to the control element to transmit a compressing force and a tensioning force applied by the control element to the clip chain, each of the clips including a pair of opposed jaws moveable between open and closed positions, the magazine further including a clip limiting feature distally past which only a distal-most one of the clips may pass, a relief portion of the magazine permitting separation of the most distal clip from the clip chain when the distal end of a clip immediately proximal to the distal-most clip is located therein, the clips being biased so that, when a distal-most one of the clips is moved distally out of the magazine, arms of the distal-most clip move apart to a tissue receiving configuration, a distal opening of the magazine being shaped so that, as the distal-most clip is drawn back into the opening through the application of tension to a proximal-most clip of the clip chain, the clip arms of the distal-most clip are drawn together to grip tissue received therebetween.

9. The apparatus according to claim 8, wherein the magazine is flexible for bending with respect to a longitudinal axis thereof.

10. The apparatus according to claim 8, wherein each of the clips comprises a proximal linking feature graspable by the jaws of an immediately proximal clip.

11. The apparatus according to claim 10, wherein the distal-most clip is releasable by opening the jaws of immediately proximal clip when the immediately proximal clip is located in the relief portion of the magazine.

12. The apparatus according to claim 11, wherein the relief portion comprises one of a cutout in a wall of the magazine, a flexible portion of the wall of the magazine and a moveable tab formed in the wall of the magazine.

13. The apparatus according to claim 8, wherein the clip limiting feature comprises a reduced cross section portion of the magazine.

14. The apparatus according to claim 13, wherein the reduced cross section portion is sized to allow translation therethrough of a clip with closed jaws and to prevent translation therethrough of a clip with partially open jaws.

15. The apparatus according to claim 8, wherein the magazine comprises an anti-pull back tab limiting proximal movement of the distal-most clip.

16. The apparatus according to claim 15, wherein the anti-pull back tab limits proximal movement of a lock ring of the distal-most clip.

17. The apparatus according to claim 16, wherein the anti-pull back tab cooperates with the lock ring to lock the distal-most clip in a closed configuration.

18. The apparatus according to claim 8, wherein the clip limiting feature sets a maximum distal displacement of the clip chain.

19. The apparatus according to claim 8, wherein the relief portion, during a proximal movement of the control element, causes proximal movement of the clip arms of the clip immediately proximal to the distal-most clip of the clip chain, the proximal movement separating the distal-most clip from the immediately proximal clip coupled thereto.

20. The apparatus according to claim 19, wherein the proximal movement of the clip arms of the clip immediately proximal to the distal-most clip of the clip chain release the distal-most clip from the clip chain.

21. A method of deploying hemostatic clips, comprising:
   inserting to a target site in a body a magazine including a plurality of hemostatic clips connected in a clip chain, each of the clips including a pair of opposed arms;
   translating the clip chain distally to extend a distal-most one of the clips out of a distal end of the magazine to open the clip arms of the distal-most clip into a tissue receiving configuration;
   positioning the distal-most clip to receive a first target portion of tissue between the clip arms thereof;
   translating the clip chain proximally to draw the distal-most clip back into the magazine and close the clip arms of the distal-most clip over the first target portion of tissue, the translating being performed by applying a tensioning force to a proximal-most clip of the clip chain;
   translating the clip chain further proximally to detach the distal-most clip from a next most distal clip of the clip chain; and
   moving the magazine to a second target location to deploy the next most distal clip over a second target portion of tissue.

22. The method according to claim 21, further comprising inserting the magazine to the target site through an endoscopic instrument.

23. The method according to claim 21, wherein the clip chain is translated distally and proximally by manipulating a handle coupled to a control element extending from the handle to a proximal-most one of the clips of the clip chain.

24. The method according to claim 21, further comprising placing a lock ring on the clamped most distal clip to lock clip arms of the distal-most clip closed.

25. The method according to claim 21, further comprising detaching the most distal clip by partially opening clip arms of a next most distal clip.

* * * * *